United States Patent
Keane

(10) Patent No.: US 11,051,748 B2
(45) Date of Patent: Jul. 6, 2021

(54) MULTIPLE FREQUENCY NEUROFEEDBACK BRAIN WAVE TRAINING TECHNIQUES, SYSTEMS, AND METHODS

(71) Applicant: 40 Years, Inc., Kenmore, WA (US)

(72) Inventor: Christopher Keane, Kent, WA (US)

(73) Assignee: 40 YEARS, INC., Kenmore, WA (US)

( * ) Notice: Subject to any disclaimer, the term of this patent is extended or adjusted under 35 U.S.C. 154(b) by 251 days.

(21) Appl. No.: 16/044,494

(22) Filed: Jul. 24, 2018

(65) Prior Publication Data

US 2020/0069208 A1 Mar. 5, 2020

(51) Int. Cl.
*A61B 5/0482* (2006.01)
*A61B 5/16* (2006.01)
(Continued)

(52) U.S. Cl.
CPC .............. *A61B 5/375* (2021.01); *A61B 5/168* (2013.01); *A61B 5/378* (2021.01); *A61B 5/38* (2021.01);
(Continued)

(58) Field of Classification Search
CPC . A61B 5/1118; A61B 5/7225; A61B 5/04842; A61B 5/4064; A61B 5/6803; A61B 5/7267; A61B 5/7405; A61B 2503/12; A61B 5/0482; A61B 5/168; A61B 5/7203; A61B 5/04845; A61B 5/742; A61B 5/7257; A61B 5/048; A61B 5/6814;
(Continued)

(56) References Cited

U.S. PATENT DOCUMENTS

| 4,928,704 A | 5/1990 | Hardt |
| 5,443,076 A | 8/1995 | Bau |

(Continued)

FOREIGN PATENT DOCUMENTS

WO      WO 01/08125      2/2001

OTHER PUBLICATIONS

"A Beginner's Guide to Recurrent Networks and LSTMs," Skymind, 2017, retrieved from the Internet at https://deeplearning4j.org/lstm.html on Jul. 1, 2018, 15 pages.

(Continued)

*Primary Examiner* — Christine H Matthews
*Assistant Examiner* — Joshua Daryl D Lannu
(74) *Attorney, Agent, or Firm* — Knobbe, Martens, Olson & Bear, LLP

(57) ABSTRACT

Methods, systems, and techniques for providing neurofeedback and for training brain wave function are provided. Example embodiments provide a Brain Training Feedback System ("BTFS"), which enables participants involved in brain training activities to learn to evoke/increase or suppress/inhibit certain brain wave activity based upon the desired task at hand. In one embodiment, the BTFS provides a brain/computer interaction feedback loop which monitors and measures EEG signals (brain activity) received from participant and provides feedback to participant. The BTFS may use an FFT based system or machine learning engines to deconstruct and classify brain wave signals. The machine learning based BTFS enable optimized feedback and rewards, adaptive feedback, and an ability to trigger interventions to assist in desired brain transitions.

27 Claims, 19 Drawing Sheets

(51) Int. Cl.
| | |
|---|---|
| A61B 5/0484 | (2006.01) |
| A61B 5/00 | (2006.01) |
| A61B 5/375 | (2021.01) |
| A61B 5/38 | (2021.01) |
| A61B 5/378 | (2021.01) |
| A61M 21/02 | (2006.01) |
| A61B 5/11 | (2006.01) |

(52) U.S. Cl.
CPC .......... *A61B 5/6803* (2013.01); *A61B 5/7225* (2013.01); *A61B 5/7267* (2013.01); *A61B 5/1118* (2013.01); *A61B 5/165* (2013.01); *A61B 5/4064* (2013.01); *A61B 5/7203* (2013.01); *A61M 21/02* (2013.01)

(58) Field of Classification Search
CPC ....... A61B 5/746; A61B 5/165; A61B 5/7264; A61M 2205/3553; A61M 2205/3592; A61M 2205/505; A61M 21/02; A61M 2205/702; A61M 21/0094; A61M 2230/10; A61M 2021/0044; A61M 2205/3584; A61M 2021/0027; A61M 2205/3561; A61M 2205/02; A61M 2021/0055; A61M 2210/0693; A61M 2021/0072; A61M 2205/587; A61M 2021/0022; A61M 2210/0687; A61M 2230/005; G16H 20/70
See application file for complete search history.

(56) References Cited

U.S. PATENT DOCUMENTS

| | | | |
|---|---|---|---|
| 8,005,691 | B2 | 8/2011 | Kumar et al. |
| 2002/0198473 | A1 | 12/2002 | Kumar et al. |
| 2007/0266273 | A1 | 11/2007 | Adachi et al. |
| 2009/0287108 | A1 | 11/2009 | Levy |
| 2011/0028827 | A1 | 2/2011 | Sitaram et al. |
| 2014/0242559 | A1 | 8/2014 | Patel |
| 2015/0342493 | A1* | 12/2015 | Hardt ................ A61B 5/0482 600/545 |
| 2016/0005320 | A1 | 1/2016 | deCharms et al. |
| 2016/0005323 | A1* | 1/2016 | Nkambou ............... G06N 5/04 434/353 |
| 2016/0082222 | A1 | 3/2016 | Garcia Molina et al. |
| 2016/0243701 | A1* | 8/2016 | Gildert ................ G05B 19/42 |
| 2019/0096281 | A1 | 3/2019 | Ahmad |

OTHER PUBLICATIONS

"Micropower, Zero Drift, True Rail-to-Rail Instrumentation Amplifier," Analog Devices, Inc., Data Sheet, AD8237, 2012, last content update Feb. 23, 2017, 29 pages.

Gers, Felix A. et al., "Learning to Forget: Continual Prediction with LSTM," Abstract, ACM Digital Library, 2018, 2 pages.

Gers, Felix A. et al., "Learning to Forget: Continual Prediction with LSTM," IDSIA, Lugano, Switzerland, 2000, 20 pages.

Goodman, "The Promise and Perils of Brain Training," WebMD, Dec. 11, 2014, retrieved from the Internet through https://www.webmd.com/special-reports/brain-training/20141211/brain-training-promise-. . . on Mar. 19, 2018, 10 pages.

Hochreiter et al., "Long Short-Term Memory," Neural Computation 9(8):1735-1780, 1997.

McKnight et al., "Attention and Neurofeedback Synchrony Training: Clinical Results and Their Significance," J. of Neurotherapy, vol. 5(1/2), 2001, 14 pages.

"Neurofeedback," Wikipedia, retrieved from the Internet through https://en.wikipedia.org/wiki/Neurofeedback on Mar. 19, 2018, 7 pages.

Nuwer, "Assessment of digital EEG, quantitative EEG, and EEG brain mapping: Report of the American Academy of Neurology and the American Clinical Neurophysiology Society," American Academy of Neurology, Neurology 1997;49:277-292.

Othmer, "Restoring the Brain," CRC Press, Taylor and Francis Group, Boca Raton, Florida, 2016, Chapter 2, "History of the Development of Neurofeedback," 30 pages.

Putman, "Signal Processing Techniques," EEG Info, www.eeginfo.com, 2007, 16 pages.

"Recurrent Neural Networks," TensorFlow, retrieved from the Internet at https://www.tensorflow.org/tutorials/recurrent on Jul. 1, 2018, 4 pages.

Teplan, "Fundamentals of EEG Measurement," Institute of Measurement Science, Slovak Academy of Sciences, Bratislava, Slovakia, Measurement Science Review, vol. 2, Section 2, 2002, 11 pages.

"Understanding LSTM Networks," colah's blog, retrieved from the Internet at https://colah.github.io/posts/2015-08-Understanding-LSTMs/ on Jul. 1, 2018, 9 pages.

10/20 System Positioning Manual, Trans Cranial Technologies Ltd., Hong Kong, 20 pages.

International Search Report and Written Opinion for International Application No. PCT/US2019/041722, dated Oct. 31, 2019, in 7 pages.

Chapin, et al., Neurotherapy and Neurofeedback: Brain-Based Treatment for Psychological and Behavioral Problems, page from Chapter 6, dated 2014, in 3 pages.

\* cited by examiner

MULTIPLE FREQUENCY NEUROFEEDBACK BRAIN WAVE TRAINING TECHNIQUES, SYSTEMS, AND METHODS

TECHNICAL FIELD

The present disclosure relates to methods, techniques, and systems for providing neurofeedback and for training brain wave function and, in particular, to methods, techniques, and systems for artificial intelligence-assisted processing and monitoring of brain wave function and optimization of neurofeedback training.

BACKGROUND

Neurofeedback has been used as a biofeedback mechanism to teach a brain to change itself based upon positive reinforcement through operant conditioning where certain behaviors, for example, the brain being in a desired state of electrical activity, are rewarded. To reward desired brain wave activity, biofeedback in the form of an appropriate visual, audio, or tactile response is generated. For example, some applications use a particular discrete sound like a "beep" or "chime" or use, for example, a desired result in a video game. Neurofeedback has been used for both medical and non-medical, research and clinical purposes, for example to inhibit pain, induce better performance, focused attention, sleep, or relaxation, to alleviate stress, change mood, and the like, and to assist in the treatment of conditions such as epilepsy, attention deficit disorder, and depression.

Typical neurofeedback uses a brain/computer interface to detect brain activity by taking measurements to record electroencephalogram ("EEG") activity and rewards desired activity through some type of output. EEG measures changes in electric potentials across synapses of the brain (the electrical activity is used to communicate a message from one brain cell to another and propagates rapidly). It can be measured from a brain surface using electrodes and conductive media attached to the head surface of a participant (or through internally located probes). Once measured, the EEG activity can be amplified and classified to determine what type of brain waves are present and from what part of the brain based upon location of the measurement electrodes, signal frequency patterns, and signal strength (typically measured in amplitude). In some scenarios, Quantitative EEG ("QEEG"), known also as "brain mapping" has been used to better visualize activity (for example using topographic and/or heat map visualizations) in the participant's brain while it is occurring to determine spatial structures and locate errors where the brain activity is occurring. In some cases, QEEG has been used to assist in the detection of brain abnormalities.

To date, neurofeedback use for training a participant's brain ("brain training") has been restricted to training one modality (brain wave classification type or other desired kind of activity) at a time. Typically, a Fourier Transform (or Fast Fourier Transform, known as an "FFT") is used to transform the raw signal into a distribution of frequencies so that brain state can be determined. The large amount of data received from an individual EEG recording can present lots of difficulties to effective measurement. M. Teplan, *Fundamental of EEG Measurement*, in Measurement Science Review, Vol. 2, Sec. 2, 2002, provides a detailed background of EEG measurement. Some of the problems that exist with current technologies include that many samples are required to obtain sufficient data, it is difficult to obtain the data timely, the data may be polluted or distorted by impedance or background (or other bodily function) noise and thus achieving an acceptable signal-to-noise ration may be difficult. For example, it may be desirable to reduce both patient and technology related artifacts, such unwanted body movements and AC power line noise, to obtain a clearer signal. Further, the storage requirements for the signal data may be overwhelming for an application. For example, one hour of eight channels of 14-bit signal sampled at 500 hertz (Hz) may occupy 200 Megabytes (MB) of memory. (Id. at p. 9.)

DETAILED DESCRIPTION

Figure 1:
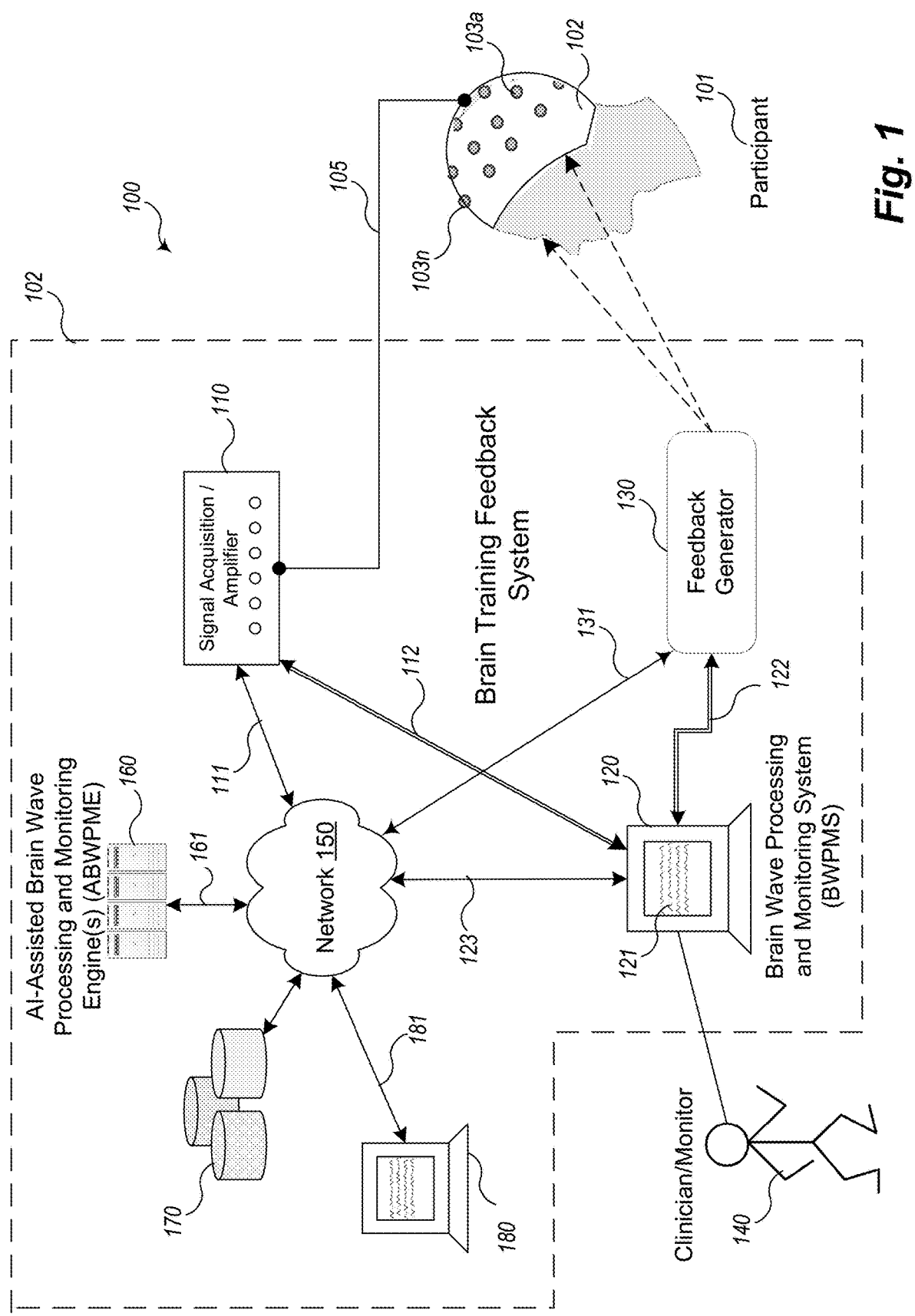
FIG. 1 is a block diagram of an example Brain Training Feedback System environment implemented using example Brain Wave Processing and Monitoring Systems and/or example Artificial Intelligence (AI)-Assisted Brain Wave Processing and Monitoring Engines.

Embodiments described herein provide enhanced computer- and network-based methods, techniques, and systems for providing neurofeedback and for training brain wave function. Example embodiments provide a Brain Training Feedback System ("BTFS"), which enables participants involved in brain training activities to learn to evoke/increase or suppress/inhibit certain brain wave activity based upon the desired task at hand. For example, the participant may desire to train to more consistent and powerful use of alpha waves, commonly associated with non-arousal such as relaxation or reflectiveness (but not sleeping). The BTFS provides a feedback loop and a brain/computer interface which measures, classifies, and evaluates brain electrical activity in a participant from EEG data and automatically provides biofeedback in real-time or near real-time to the participant in the form of, for example, audio, visual, or tactic (haptic) output to evoke, reinforce, inhibit, or suppress brain activity responses based upon a desired goal.

For the purposes of this disclosure, "real time" or "real-time" refers to almost real time, near real time, or time that is perceived by a user as substantially simultaneously responsive to activity. Also, although described in terms of human participants, the techniques used here may be applied to other mammalian subjects other than humans.

Example embodiments provide a Brain Training Feedback System which provides improvements over prior techniques by allowing for the simultaneous or concurrent training of multiple modalities (target brain wave training or desired brain-related events) and the training of "synchrony" for a specific frequency or set of frequencies. Synergistic outcomes are possible with multiple frequency training. Here, synchrony refers to the production of the waveform coherence (same desired brain activity) at multiple (two or more) different locations of the brain at the same time. The locations may be located in different hemispheres (left and right, side to side), or they may be located front and back. In some scenarios, concurrent or simultaneous training of multiple modalities can facilitate parallel development of new neural pathways in the brain of the participant at a linear rate equivalent to the single modality training multiplied by the number of modalities trained. The BTFS also provides improved results over classic neurofeedback systems by incorporating the use of customized soundtracks (and not just discrete sounds lacking contextual data). Customized soundtracks improve the brain training process by continuous modulation of incentive salience and dopamine release by providing the brain being trained with a pleasing and continuous reward that varies in intensity according to the subject brain's own performance. The customized soundtracks enable the training of multiple modalities by providing discrete but aurally integrated rewards across modalities. In addition, BTFS examples can incorporate surround sound to give precise feedback to a participant regarding the source location of one or more signals. Current neurofeedback systems do not provide this information to participants in audio form. This feature improves the brain training process by providing directional detail to the brain being trained about the action performed that produced a reward. This allows the subject brain to more accurately and rapidly discern the discrete action that is being rewarded.

In addition, example Brain Training Feedback Systems overcome the challenges of prior computer implementations used for neurofeedback by incorporating machine learning techniques where and when desired. Machine learning can be incorporated by components of the BTFS to perform one or more of the following activities:

deconstruct (decompose or filter) and classify signal data for improved real time performance and accuracy and using less expensive equipment, because machine learning algorithms can perform signal classification with fewer EEG data samples and can function at a slower sampling rate enabling incorporation of less expensive and/or less complex amplifiers/AD converters;

model brain wave signal patterns for each participant on a customized basis which is capable of adapting over time as the participant's EEG behavior changes (as the brain "learns/improves");

enable multiple brain wave modality training simultaneously;

selectively choose feedback rewards and optimize feedback generation on a per-participant basis, which is optimized for the participant based upon individualized responses and can be adapted over multiple sessions or over time;

provide participant customized and automated artificial intelligence (AI)-assisted "boosting" to enhance the brain training, for example, to trigger a desired response at particular times or responsive to particular conditions based upon the modeled signal patterns and by selective or concurrent application of other stimuli (such as flashing lights, applying electromagnetic stimulation or transcranial direct current stimulation (tDCS)—low voltage current, audio, or silence).

Other uses are contemplated.

Also, although machine different types of machine learning engines and algorithms can be used, in one example scenario, the BTFS uses a long short term memory (LSTM) recurrent neural network (RNN) to customize electrode mapping, to customize feedback generation for a participant, and to provide automated AI-assisted boosting. Incorporation of LSTMs provides vast efficiency enhancements over FFT techniques, because signal input can be processed and results output for each inputted raw signal—it is not necessary to collect a large multiple of samples (e.g., 256) to derive output ever 1 or 2 seconds. See, e.g., *A Beginner's Guide to Recurrent Networks and LSTMs*, found online at "deeplearning4j.org," downloaded Jul. 1, 2018; Colah, *Understanding LSTM Networks*, posted online at "colah.github.io/posts/2015-08-Understanding-LSTMs," downloaded Jul. 1, 2018; GOOGLE, *Tutorial on Recurrent Neural Networks*, posted online at TENSORFLOW (open source) website "tensorflow.org/tutorials/recurrent," downloaded Jul. 1, 2018; and Hochreiter and Schmidhuber, *Long Short-Term Memory*, Neural Computation, Volume 9, Issue 8, p. 1735-1780 (1997); which provide background on LSTMs and RNNs. The LSTMs of example BTFSes produce output and feedback generation at a much faster rate than FFTs thus improving accuracy and timeliness of the feedback to the participant, which ultimately improves the speed and efficacy of brain training.

Whereas current neurofeedback systems are expensive and complex to use (often requiring highly trained technicians and clinicians), the incorporation of these features into example Brain Training Feedback Systems enables provisioning of low cost, easy-to-use, home-based neurofeedback systems by storing massive amounts of data and performing computationally intensive processing over the network using streamed sequences of EEG data. The pipelined architecture of LSTM brain training engines (and models) enable this type of processing.

FIG. 1 is a block diagram of an example Brain Training Feedback System environment implemented using example Brain Wave Processing and Monitoring Systems and/or example Artificial Intelligence (AI)-Assisted Brain Wave Processing and Monitoring Engines of the present disclosure. The BTFS environment 100 provides a brain/computer interaction feedback loop which monitors and measures EEG signals (brain activity) received from participant 101 via electrodes 103a and 103n of electrode cap 102 and provides feedback to participant 101 via feedback generator 130. The feedback generated by feedback generator 130 may be visual, audio, or tactile and may comprise multiple subsystems, screens, displays, speakers, vibration or touch devices or the like. The Brain Training System 102 itself refers to one or more of the computer or electrical components shown in the BTFS environment 100—depending upon whether certain components are provided external to the BTFS by others (e.g., third parties, existing systems, etc.).

For example, one form of the BTFS 102 (which uses FFT technology) uses Brain Wave Processing and Monitoring System (BWPMS) 120 and signal acquisition/amplifier 110 via paths 105 and 112, respectively, to acquire, deconstruct, and analyze/classify signals received. The signal is amplified (and optionally analog filtered) by signal amplifier 110, which converts the analog signal to digital format using one or more A/D converters and passes the digital signal along path 112 to the BWPMS 120. The BWMPS 120 further transforms and/or processes the signal into its constituent frequencies, potentially applying digital filtering to isolate aspects of the signal and/or to remove artifacts. The processed signal data is then stored locally as part of the BWPMS 120 or remotely in data repositories 170 connected via network 150 (for example, the Internet). Network 150 may be wired or wireless or a wide-area or local-area (or virtual) network. Based upon the desired training (e.g., the designated modality), the BWMPS 120 determines what type of feedback to generate based for example on prior session configuration parameters and causes generation of the determined feedback via feedback generator 130. Through this neurofeedback process, the brain training is effectuated and the participant "learns" (unconsciously) to adjust brain activity.

Another form of the BTFS 102 incorporates machine learning and artificial intelligence techniques to deconstruct and analyze or classify received EEG signals (brain activity) from participant 101 via amplifier 110 and to cause feedback to participant 101 via feedback generator 130. In this BTFS form, paths 112 and 122 (labeled by double lines) are replaced by communication paths 111, 161, and 123 (labeled by single lines) that are network connected via network 150. A set of AI-Assisted Brain Wave Processing and Monitoring Engines (ABWPME) 160, which are connected to the BTFS environment 100 via path 161, provide a plurality of models (one or more of the same or using different machine learning algorithms) for deconstructing, analyzing or classifying amplified signals received via communication path 111 into processed signal data (which is stored in data repositories 170). Depending upon the particular BTFS 102 or BTFS environment 100 configuration, the ABWPE 160 components may be hardware, software, or firmware components of a single or virtual machine, or any other architecture that can support the models. A separate (distinct) ABWPE 160 component may be allocated based upon participant, session, channel (electrode source), signal modality, or the like. The ABWPE 160 components are also responsible for determining and causing feedback to be provided to participant 101 via feedback generator 130 (and communication path 131).

Both forms of the BTFS 102 may also include components 120 and 110 network-connected for other reasons, such as to store signal data in data repositories 170 and to interact with another system or another user 180 who may, for example, be remotely monitoring the neurofeedback session via connection 181. For example, a clinician/monitor 140 or other type of system administrator may be present in either BTFS environment 100 to help interpret or facilitate the brain training activities. In addition, third parties (not shown) such as researchers or data analyzers (or merely interested observers with appropriate permissions) may be remotely monitoring the neurofeedback session via connection 181.

Figure 2:
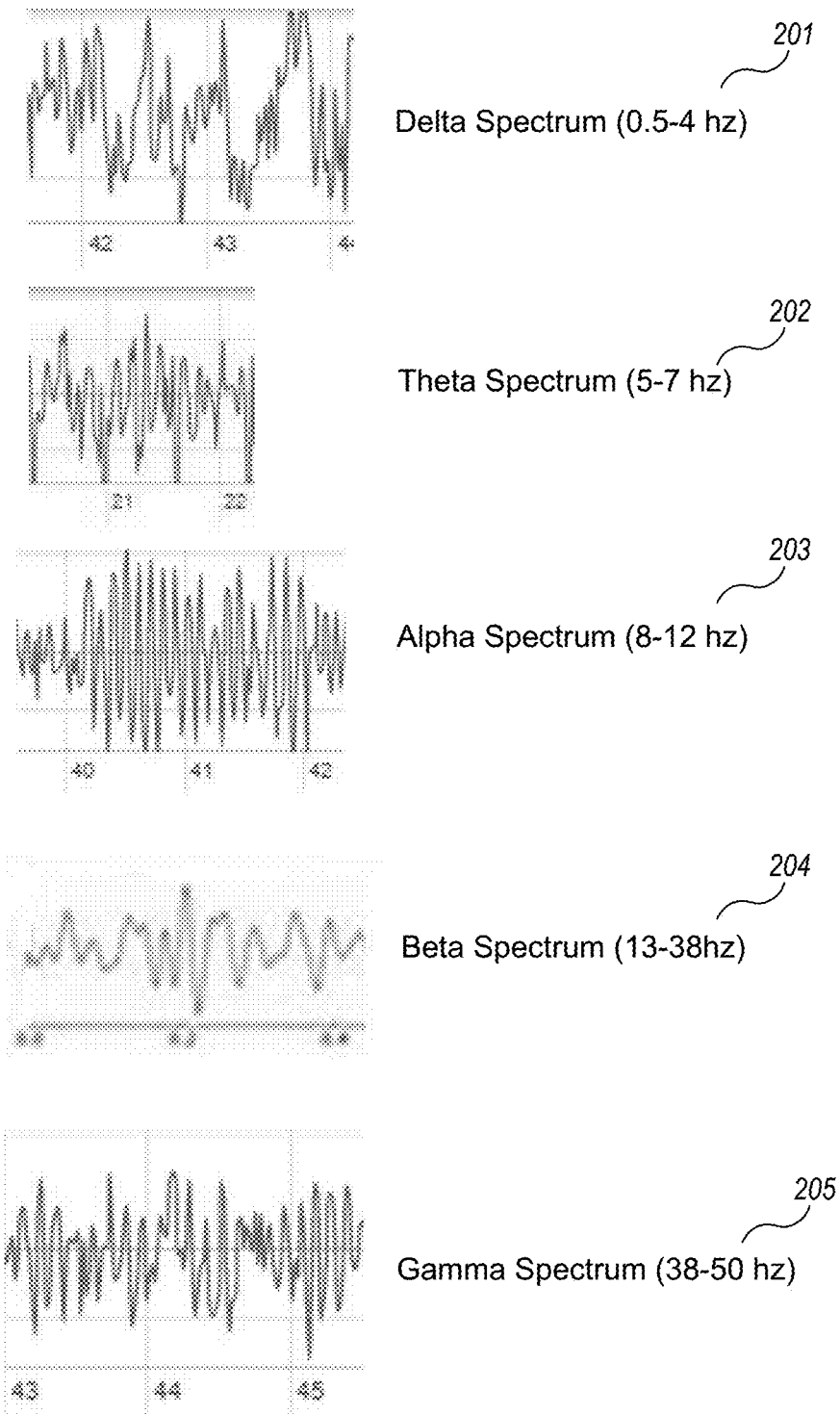
FIG. 2 is an example diagram of various types of brain waves that can be monitored by an example Brain Training Feedback System.

FIG. 2 is an example diagram of various types of brain waves that can be monitored by an example Brain Training Feedback System. For example, the brain wave signal types illustrated in FIG. 2 may be monitored by BTFS environment 100 of FIG. 1. Other types of signal patterns such as spikes, spindles, sensorimotor rhythm, and synchrony may also be monitored. Brain waves are classified according to their frequency (typically in hertz), that reflects how fast or slow they are—how many times the wave oscillates in a second, and its amplitude (typically measured in microvolts). Stronger signals result in higher amplitudes. Slower signals (fewer oscillations per second) are associated with less conscious brain activity. For example, brain signals in the delta spectrum 201 occur in the frequency range on average of 0.5-4 Hz and are associated with dreamy, visionary sleep (REM or deep sleep). Brain signals in the theta spectrum 202 occur in the frequency range on average of 5-7 Hz and are present when someone is about to go to sleep. For example, you may know you had a great idea but when you awake you can no longer remember it. Brain signals in the alpha spectrum 203 occur in the frequency range on average of 8-12 Hz and are present when someone is fully conscious but not active. It is sometimes considered the "visionary" state because it is the slowest fully conscious state which a majority of the brain population can access when awake. Many brain training applications address improvements with regard to this state. Participants are typically instructed to close their eyes to work in this modality and doing so is prone to induce a transition from beta to alpha waves. Brain signals in the beta spectrum 204 occur in the frequency range on average of 12-38 Hz and are associated with full consciousness, for example, talking, active muscle innervation, etc. Brain signals in the gamma spectrum 205 occur in the frequency range on average of 38-50 Hz and, although not well known because they occur so quickly, are associated with more focused energy. The frequency values vary somewhat depending upon the literature, but the ideas are basically the same—slower (lower) frequency of brain waves are associated with more "sleepful" lack of activity. Brain wave patterns are unique to each individual and accordingly they can be used as a kind of "fingerprint" of the participant.

Figure 3:
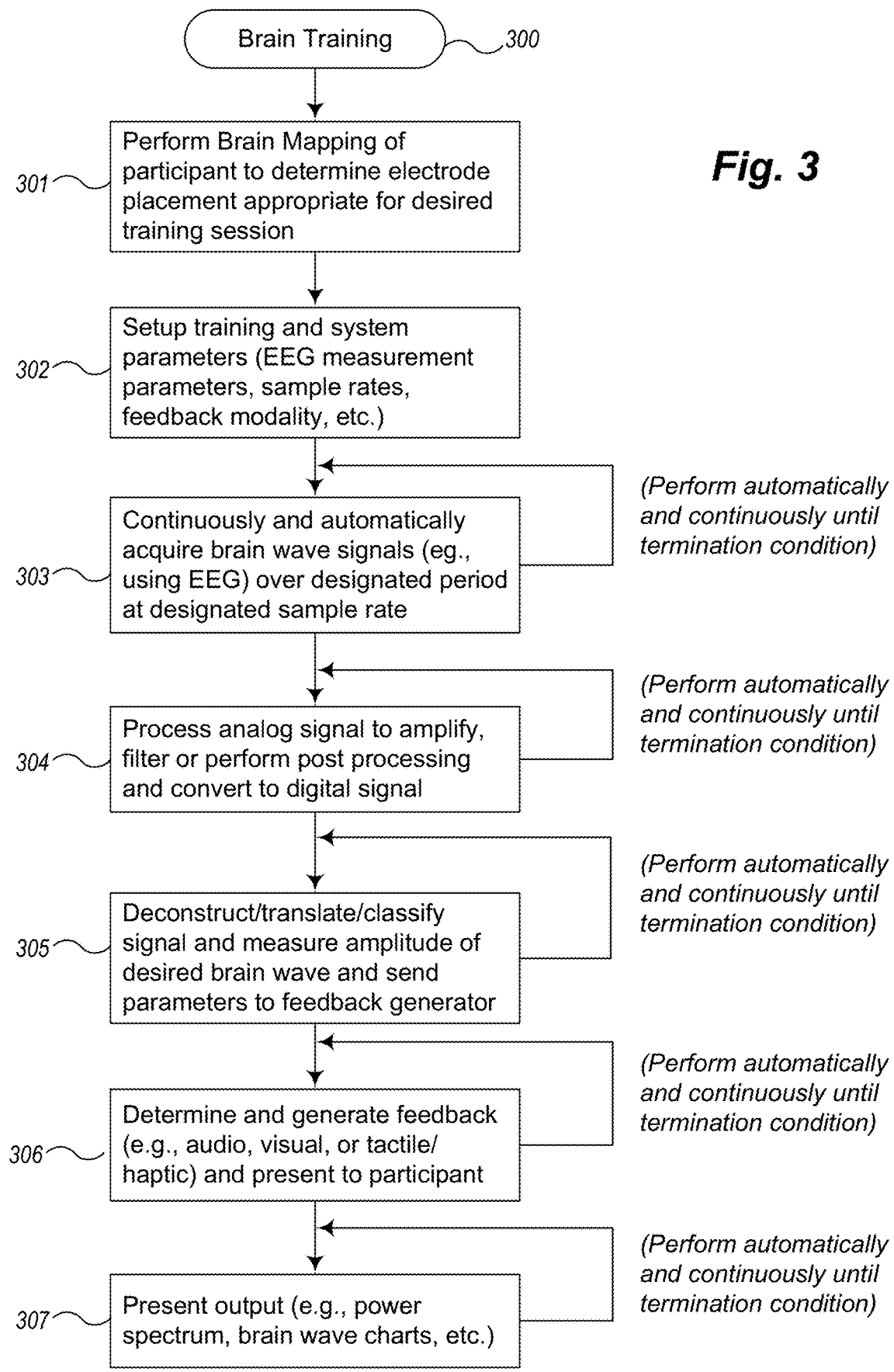
FIG. 3 is an example overview flow diagram of an example process for implementing an example Brain Training Feedback System using one or more example Brain Wave Processing and Monitoring Systems and/or example AI-Assisted Brain Wave Processing and Monitoring Engines.

FIG. 3 is an example overview flow diagram of an example process for implementing an example Brain Training Feedback System using one or more example Brain Wave Processing and Monitoring Systems and/or example AI-Assisted Brain Wave Processing and Monitoring Engines. For example, the logic of FIG. 3 may be implemented by the BWPMS 120 or the ABWPMEs 160 of FIG. 1. This logic is not specific to a particular component and, as discussed with reference to FIG. 1, may be performed by different components and distributed depending upon the particular configuration of the BTFS.

For example, in block 301, the BTFS determines electrode placement for a particular brain training session. A session is indicative of a particular time that a participate uses the neurofeedback system for brain training. Its duration may be determined in seconds, minutes, hours, or days. Typically, a session constitutes a length of time of approximately ninety minutes. A brain training session is associated with a particular signal modality (frequency, event, or set of modalities). For example, a session may be for "alpha wave training" or for "synchrony of alpha and theta," etc. Once this training objective is set, it is possible to determine electrode placement. In some cases, an administrator (clinician, observer, monitor, etc.) performs what is known in the industry as "brain mapping" to determine desired electrode placement. In some cases, quantitative EEG (qEEG) visualization and brain mapping is used using an 18-channel qEEG/LORETA (low resolution electromagnetic tomography) helmet to obtain an initial picture of how the participant's brain is working before engaging in brain training using the BTFS.

Any type of electrodes may be integrated with the BTFS systems described herein; however, example BTFS systems are currently implemented with silver-silver chloride electrodes with conductive material (wet electrodes). Other implementations (wet and dry) are supported. Also, in the examples described herein, the electrode placement is performed by activating particular electrodes in, for example, an electrode helmet/cap such as cap 102 of FIG. 1. In current examples, four (4) electrode placements are operative, with a ground electrode, and a reference electrode. A ground electrode is typically placed on the forehead. A reference electrode, typically placed at the mastoid process (behind the ear), is used to provide the potential differential which constitutes the EEG measurement. Thus, each participant is associated with four associated channels (the active electrodes) being measured at 200 Hz to 10000 Hz, depending upon the application, in a particular session. With the advent of better processing techniques available through machine learning BTFS examples as discussed below, it is contemplated that a BTFS could handle more channels of signals at once, for example, six (6). Many current neurofeedback systems use 2 channels. Four channels provide good audio special separation for 7.1 surround sound applications used with BTFS examples. Some applications are contemplated with 6 channels.

The electrodes may be arrangement according to any scheme. Typical schemes follow the standardized International 10-20 (10/20) System which specifics placement and distances between electrodes. An alternative system, the 10-10 (10/10) System may also be used. (The second 10 or 20 refers to percentage distances between the landmarks used to place electrodes.) This standard is used to help consistency of placement of electrodes. Common placements for the electrodes include:

F3-F4-P3-P4
C3-C4-P3-P4
Fz-Pz-P3-P4
Cz-Pz-P3-P4

F stands for Frontal, T for Temporal, C, for Central, P for Parietal, and O for Occipital lobe. The number refers to a position, namely even numbers for right hemisphere and odd numbers for left. A further description of these locations is found in Trans Cranial Technologies Ltd., 10/20 *System Positioning Manual*, Hong Kong, 2012. Ground is typically located on either left or right forehead at or close to Fp1 or Fp2. Reference is typically placed at either the left or right mastoid process (behind the ear). Different placements can be used to stimulate different brain activity. For example, a brain that shows a lot of central but low front alpha may benefit from a F3/F4 placement rather than a C3/C4 placement to stimulate the brain to bring alpha forward. As another example, a brain with well distributed alpha may benefit from a Fz/Pz placement to encourage coherence and synchrony.

In a machine learning assisted implementation of the BTFS, it is contemplated that trained models can also be used to determine optimal placement of electrodes for a participant in return sessions. That is, if training has not been as effective as predicted, the ABWPMEs 160 can include models for determining and testing different electrode placement schemes.

The logic of block 302 sets up training and system parameters including what frequencies are to be monitored, sample rates (how frequent are the signal measurements taken), starting feedback modalities etc. As explained further below, there are many techniques that can be incorporated to determine the feedback modalities including administrator set, participant set, and determined automatically by one or more of the ABWPME 160 engines. The feedback modalities may incorporate audio, sound, or haptic (tactile) feedback. For example, in some instances, the participant is shown a visual representation (for example a spectral chart of frequencies) during the session. In other instances, light is used. In yet other instances and typically for the BTFS, a soundtrack is determined that is specifically targeted for the signal modality being trained. For example, different soundtrack motifs may be stored in a library and from these a motif is selected for a particular individual. For example, according to a storm motif, rain, wind, and thunder sounds may be used to give (separate) feedback for alpha, theta, and gamma brain activity, respectively. This way a participant's brain can get feedback of all three brain waves simultaneously. Soundtracks are typically of actual sounds like rain, wind, rolling thunder, cellos (or other orchestral musical instruments), choirs, babbling brooks, etc. Changes in amplitude within a frequency can control the volume and "density" (character) of the sound. Thus, for example, if the participant is generating stronger (more amplitude) alpha waves, then the rain may be louder than the wind and thunder sounds.

Logic blocks 303-307 happen continuously and are typically executed by different BTFS components in parallel. Thus, they are indicated as being performed automatically and continuously until some termination condition occurs, for example, termination of the session. As described with respect to FIG. 1, these blocks are performed by the different components including, for example, the signal acquisition/amplifier 110, the BWPMS 120 or the ABWPME (AI) engines 160, or the feedback generator 130.

In block 303, the BTFS logic continuously and automatically (through the use of the computing systems/engines and amplifier) acquires brain wave signals over the measured channels (for example, the four channels described above), for example using the signal acquisition/amplifier 110 of FIG. 1. This signal acquisition occurs over a designated period of time and at a designated rate, for example as set in block 302.

In block 304, the BTFS logic processes the analog signal to amplify, to perform analog filtering or post-processing, and to convert the raw analog signal received from the electrodes to a digital signal. This logic is typically performed by the signal acquisition/amplifier 110 of FIG. 1, which includes an A/D converter. In one example BTFS, the A/D converter is an AD8237 analog amplifier; however other amplifiers can be incorporated including custom amplifiers. In addition, the "raw" signal packets are typically stored in the data repository (for example, repository 170 of FIG. 1.) They are raw in the sense of not yet deconstructed into frequencies and analyzed/classified but they have been processed by the amplifier, and thus, some post-processing may have been performed.

In block 305, the BTFS logic receives the stored raw (A/D processed) data signals, reviews them according to a sliding window in the case of an FFT-based BTFS, deconstructs and analyzes/classifies the signal into its constituent frequencies (and amplitudes per frequencies) and other measurements and then stores the deconstructed/analyzed/classified signal data into the data repository. (In an AI-based BTFS, the logic may also review the stored raw data signals for other reasons such as for efficiency and for analyzing soundtrack performance, although this review is not needed to deconstruct the signal as discussed below.) For example, in the case of an FFT-based BTFS (such as BTFS 120), the BTFS (a server/service thereof responsible for processing a channel) stores FFT buckets of frequency data. For example, an FFT-based BTSF may generate and store a table (e.g., an array) that stores information in 0.5 Hz buckets ever 40 msec or so, for example as shown in Table 1:

TABLE 1

| Time | 0.5 Hz | 1.0 Hz | 1.5 Hz | 2.0 Hz | 2.5 Hz | 3.0 Hz | ... | 127 Hz |
|---|---|---|---|---|---|---|---|---|
| 07:25.123 | 2.2 | 4.1 | 3.7 | 2.3 | 1.2 | 4.3 | ... | 1.2 |
| 07:25.173 | 2.3 | 4.0 | 3.5 | 2.4 | 1.3 | 4.5 | ... | 1.1 |
| ... | | | | | | | | |

The values in the frequency buckets are measures of amplitude (strength of the signal) in, for example, microvolts. A large amount of raw signal data is required to generate the FFT arrays.

In some examples, the BTFS does perform additional post-processing for example to notch-filter out 50-65 Hz frequencies (corresponding to typical AC power signal in the United States) to remove undesired impedance or noise.

In the case of an AI-based BTSF, the signal is processed by one or more machine learning models and the output stored as well in the data repository 170. The output of such models, for example, using an LSTM recurrent neural net implementation is described below with reference to FIG. 12. Unlike the FFT-based BTSF, an AI-based BTSF can process single samples at a time (it learns in a streamed sequence maintaining its own internal memory) to deconstruct the signal into constituent frequencies.

In block 306, the BTFS determines what feedback to generate and based upon what parameters and causes the feedback to be presented to the participant. In block 307, the feedback is actually presented to the participant. For example, the logic for blocks 306-307 may be performed in combination with the BTFS 120 (or the ABWPMEs 160) and the feedback generator 130 of FIG. 1.

Regardless of whether it is an FFT-based or AI-based BTFS, the BTFS typically tracks multiple moving averages of signals to determine whether effectiveness of the training over time, trends, etc. These can be used to adjust the training feedback. In one example, moving averages are computed over 5, 50, and 200 samples although other moving averages may be used. This is used currently to make directional predictions such as if the 50-sample moving average (SMA) crosses the 200 SMA going up, then the current trend of the wave is up and vice-versa if the 50 SMA crosses in the other direction. The 5 SMA may be used as an indicator to set the volume of the feedback.

For example, in one example BTFS, which plays a soundtrack for brain training of a selected modality (as opposed to a discrete single tone) each soundtrack has some number of sub-tracks, for example, a low, medium, and high and the selected sub-track depends upon a calculation of training performance based upon a moving average. For example, if the participant's brain is producing 30% or less of its capacity, the low (of the selected soundtrack) is played. For example, if the soundtrack is "rain" the participant may hear a slight pitter-patter of drizzly rain. The volume of the low soundtrack depends on where the participant brain activity is occurring within in the 0%-30% range. If the activity is at 30%, the participant will hear the low soundtrack at full volume, decreasing proportionally until the sound reaches 0% volume at 0% amplitude for that brain wave signal.

Continuing this example, between 30-70%, the BTFS causes the low soundtrack to be played at 100% volume plus the medium soundtrack at a volume proportional to the where the participant brain activity is occurring within the 30-70% range. For example, when the soundtrack is rain, a heavier rain shower sound would be generated with the volume changing depending on where in the 30-70% range the amplitude of the measured and classified signal falls.

Above 70%, the BTFS causes both low and medium soundtracks to be played at full volume, plus the heavy soundtrack. The volume of the heavy soundtrack is again determined by how much above 70% the amplitude of the participant's brain activity falls. For rain, the heavy soundtrack may be, for example, a very heavy rainfall.

Other and/or different motifs, other soundtracks, and subdivisions of soundtracks can be similarly incorporated. The basic premise is to build on a soundtrack based upon the strength of the brain signal activity so that the participant's brain can detect and react to the differences. Having a soundtrack as opposed to an individual sound, also allows example BTFSes to generate and cause feedback to presented for simultaneous and concurrent modality training. For example, if a storm motif is used and rain is used to train for alpha wave performance, then wind may be used to train theta and thunder may be used to train for gamma and each can complement the other feedback. Also, in BTFS examples that use surround sound technology, feedback may be generated specific to brain signal source location. For example, the BTFS may cause feedback in the form of a torrential downpour on the front left speaker and a quiet drizzle on the rear right, corresponding to difference in amplitudes of the signals that correspond to the electrode channels associated with each of the speakers. This gives the participant's brain additional "information" not present in current systems and allows the participant to better train both strengths and weaknesses.

Also, the BTFS can adjust the soundtrack over time based upon actual performance as the participant's brain activity changes over time. For example, as a participant becomes better at producing an alpha wave, the more difficult it becomes for the participant to earn a "heavy" reward (the heavy soundtrack) because the baseline for computation of the 0-30%, 30-70%, and over 70% of possible activity changes. Conversely, the worse a participant performs, the easier it becomes to earn heavy rewards. In an example BTFS, the system uses the sample moving averages described above to perform these calculations. For example, if a participant is generating 200 SMA of 2 microvolts (uV) of alpha and then suddenly generates 3 uV, then the participant is rewarded for this substantial gain by a substantial burst of noise (volume boost). However, if the participant continues to generate the 3 uV, then the sound gradually tapers off because the 3 uV has become a new "normal" for that participant. Conversely, if a participant is generating 10 uV of alpha and then generates 11 uV, the gain results in a mild volume boost not as noticeable.

In addition to soundtracks, as described elsewhere herein, visual feedback (such as spectral charts) as well as tactile feedback (vibrations, electromagnetic shock) may also be presented to the participant.

Figure 4:
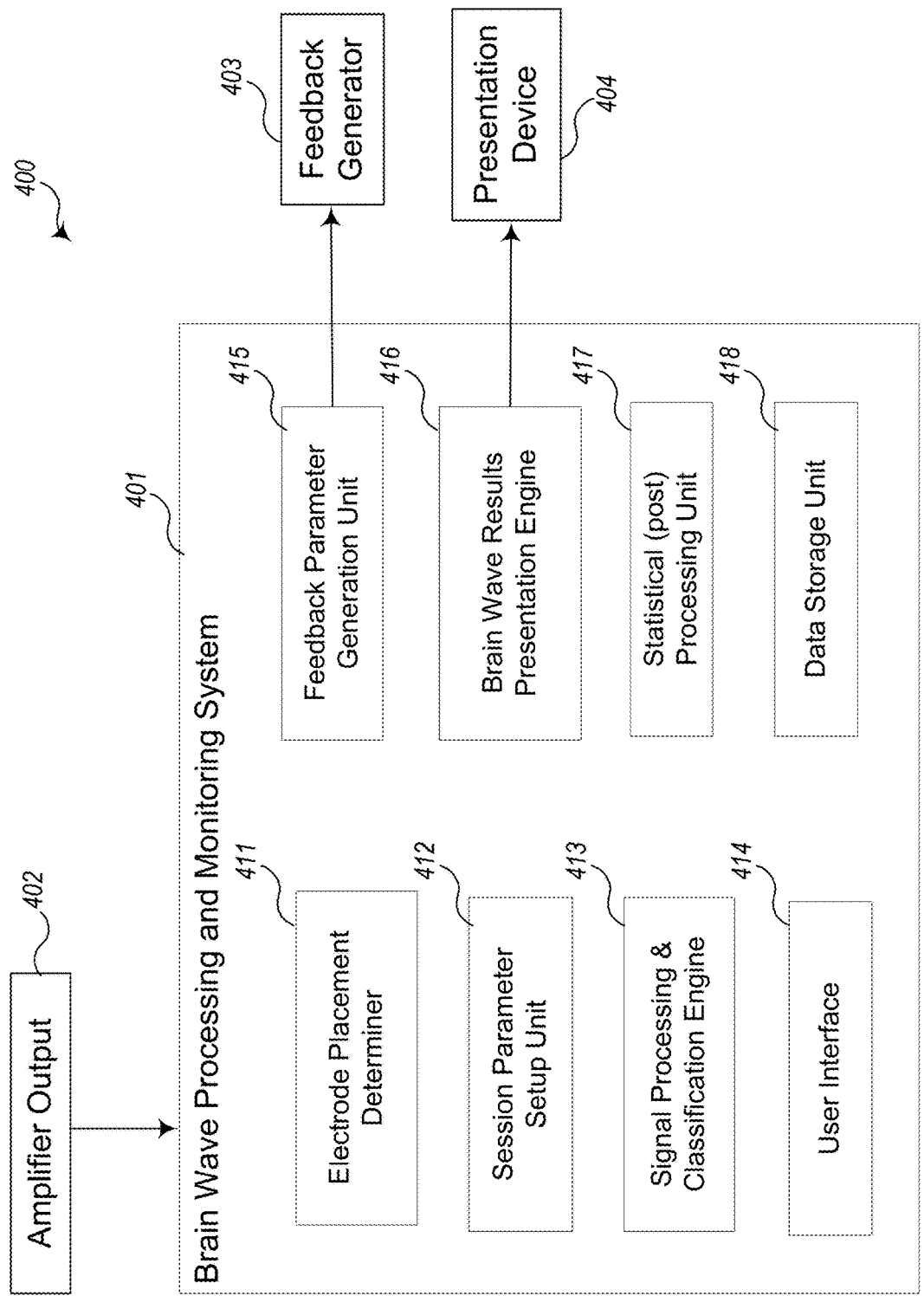
FIG. 4 is an example block diagram of components of an example Brain Wave Processing and Monitoring System.

FIG. 4 is an example block diagram of components of an example Brain Wave Processing and Monitoring System. For example, the BWPMS 120 of FIG. 1 may be implemented as shown in FIG. 4. The Brain Wave Processing and Monitoring System comprises one or more functional components/modules that work together to process digital signals on a per channel basis received from the amplifier (for example, amplifier 110 of FIG. 1). Processing may include the acts and logic described with reference to blocks 301-306 of FIG. 3. For example, a BWPMS may comprise an electrode placement determiner 411, a session parameter setup unit 412, a signal processing and classification engine 413, a user interface 414, a feedback parameter generation unit 415, a brain wave results presentation engine 416, a statistical processing unit 417, and/or a data storage unit 418. One or more of these components/modules may or may not be present in any particular embodiment.

The electrode placement determiner 411 may be used to facilitate placement of electrodes on the participant using, for example, a 10-20 (10/20) topological mapping as described above. It may retrieve and transmit to or be communicatively connected to a qEEG/LORETA device for presenting relevant information to the clinician/administrator (or whoever is responsible for making decisions of where to place electrodes).

The session parameter setup unit 412 facilitates setting up parameters such as what signal modality is being trained (e.g., what type of brain wave), desired outcomes (e.g., increase alpha wave activity), selected feedback modalities for the various frequencies and/or activity being trained (e.g., storm motif), and other information regarding the participant and session.

The signal processing and classification engine 413 performs the logic described above with reference to block 305 of FIG. 3. It receives the amplified digital signals as described via amplifier output 402, runs Fourier Transforms (FFTs) on the data to populate processed signal data for storage in data storage unit 418 or remotely, for example, in data repository 170. In some BTFSes, the processed data is stored locally and then transmitted on a periodic basis to remote storage.

Processed signals are then analyzed by the signal processing and classification engine 413 to cause the feedback parameter generation unit 415 to generate appropriate feedback parameters such as the soundtrack selection and volume attributes discussed above with reference to block 306 of FIG. 3. The feedback parameter generation unit 415 then interfaces with the feedback generator 403 (e.g., feedback generator 130 of FIG. 1) to cause the determined feedback to be generated. For example, this may cause the appropriate soundtrack to be played on speakers in the room occupied by the participant.

The user interface 414 interfaces to a user responsible for administering the system, such as a clinician, EEG technician, neurologist, etc. The interface may present display screens and implement configurations as described below with reference to FIGS. 6-9D.

Figure 9A:
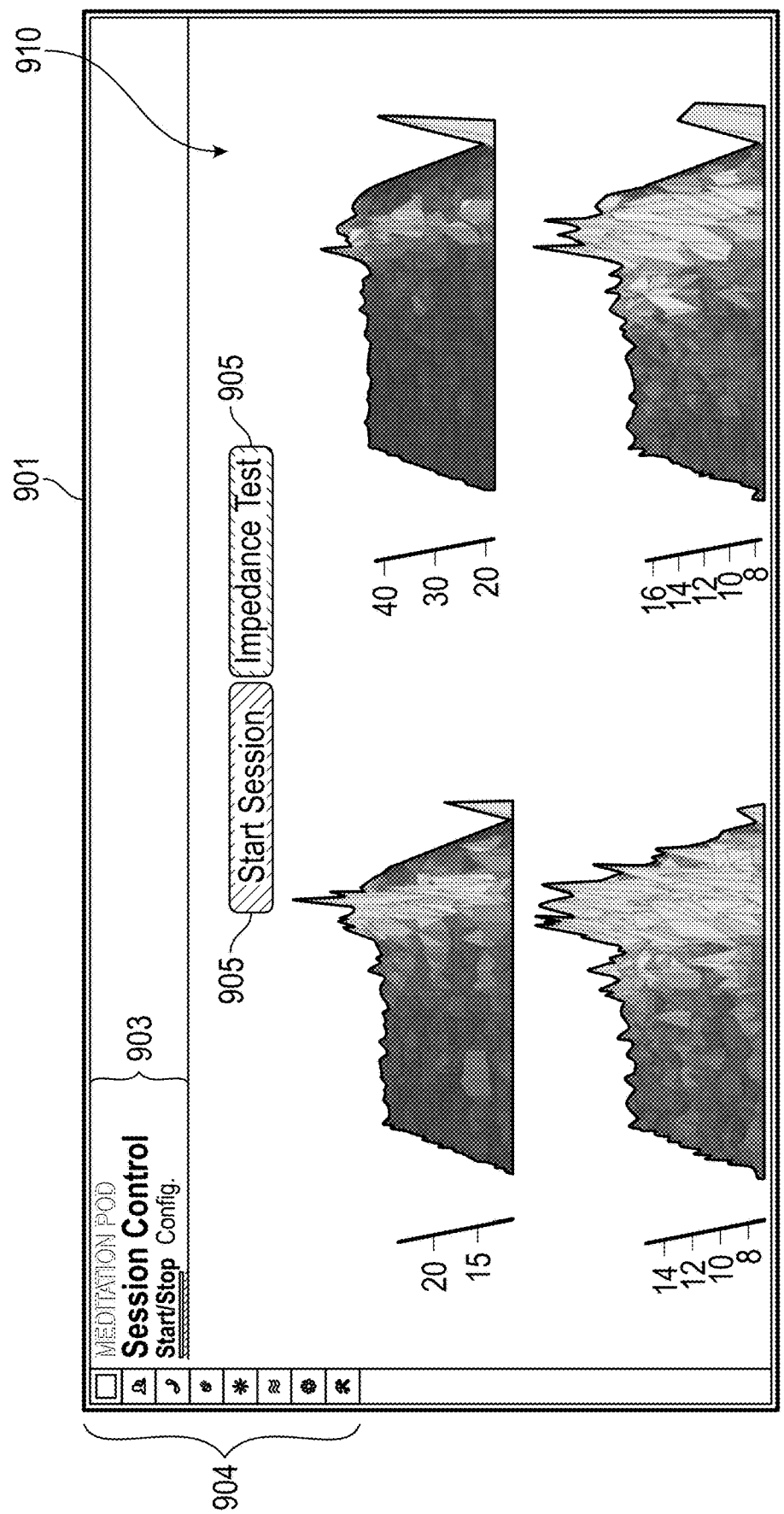
Figure 9B:
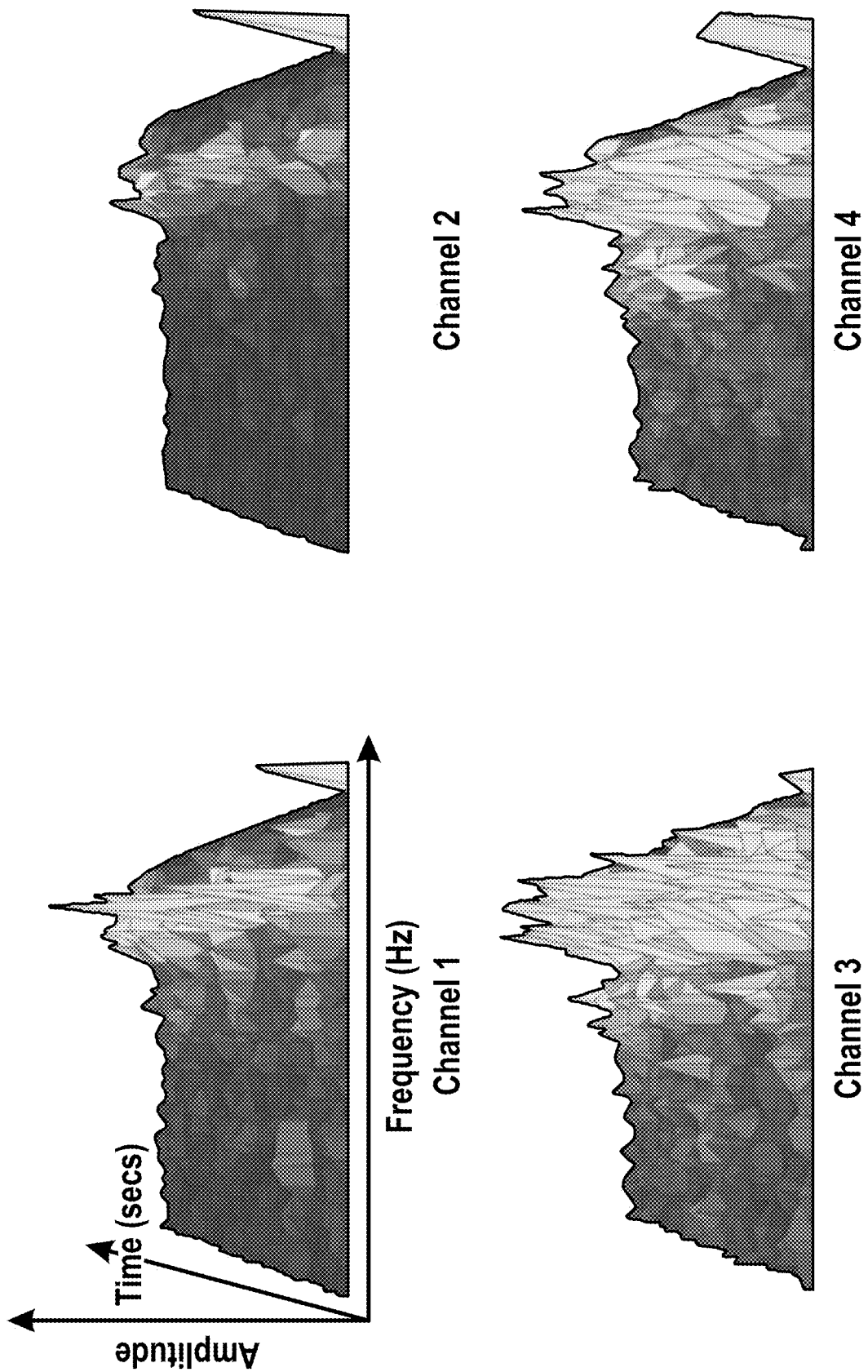

The brain wave results presentation engine 416 may optimize the presentation of graphical information such as the frequency spectral charts shown in FIGS. 9A and 9B. In some instances, these results are displayed to a participant, so the brain wave results presentation engine 416 may interface with a presentation device associated with the participant to display the desired information.

The statistical processing unit 417 provides statistical algorithms to aid processing the analyzed data and may house the sample moving average calculations and other rules used to determine feedback parameters.

Figure 5:
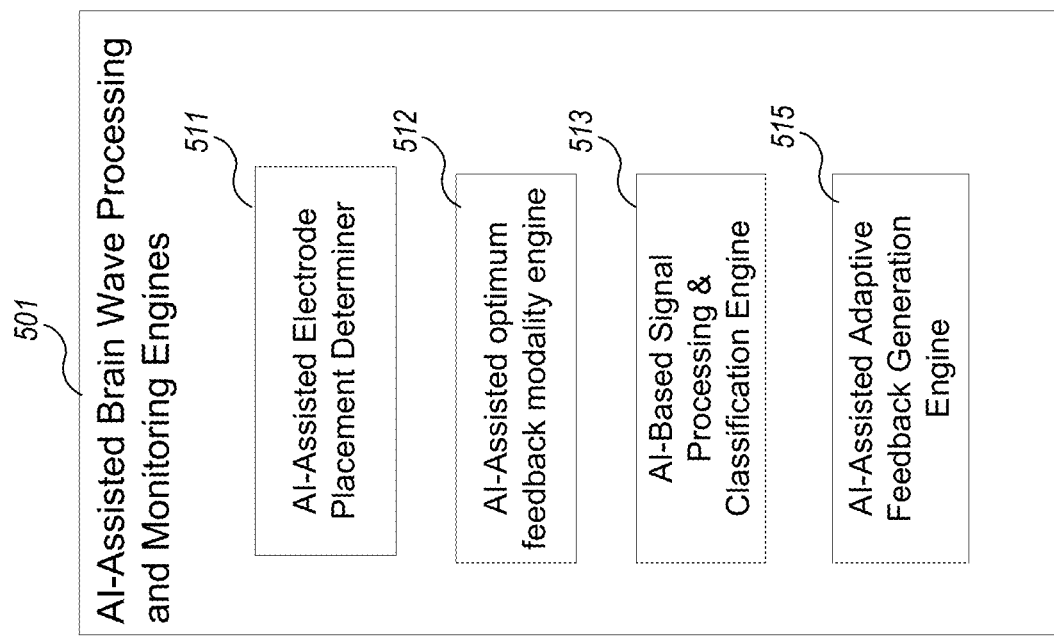
FIG. 5 is an example block diagram of components of example AI-Assisted Brain Wave Processing and Monitoring Engines.

FIG. 5 is an example block diagram of components of example AI-Assisted Brain Wave Processing and Monitoring Engines. For example, one or more of the ABWPMEs 160 of FIG. 1 may be implemented as shown in FIG. 5. The example AI-Assisted Brain Wave Processing and Monitoring Engines comprise one or more functional components/modules that work together and with the BWPMS (e.g., BWPMS 401 of FIG. 4) to process digital signals on a per channel basis received from the amplifier (for example, amplifier 110 of FIG. 1). Note that the ABWPMEs 160 are specialized machine learning modules/servers/services which work in conjunction with certain modules of the BWPMS (which can remain responsible for the user interface, storage, feedback parameter interface to the feedback generator and statistical processing) or substitute for (or supplement) other modules of the BWPMS (such as the electrode placement determiner 411, the session parameter set up 412, the signal processing and classification engine 413, and the feedback parameter generation unit 415) to provide the acts and logic described with reference to blocks 301-306 of FIG. 3.

For example, an BWPME 501 may comprise an AI-assisted electrode placement determiner 511; an AI-assisted optimum feedback modality engine 512, an AI-assisted signal processing and classification engine 513, and an AI-assisted adaptive feedback generation component 515. One or more of these components/modules may or may not be present in any particular embodiment. As described above, example BWPMEs 501 may communicate with other portions of a BTFS remotely, such as via a network (e.g., network 150 in FIG. 1).

The AI-assisted electrode placement determiner 511 is responsible for assisting in initial determination of electrode placement. Although not currently deployed, it is contemplated that as more AI-assisted brain training is performed, machine learning modules can be used in conjunction with qEEG/LORETA topological techniques to automatically designate potentially optimal electrode placement for a particular participant based upon models of other participants with similar topological brain wave activity patterns. That is, the AI-assisted electrode placement determiner 511 can use the output of qEEG mapping (showing certain factors/characteristics) and, possibly in combination with the participant's history (taken for example, at an intake interview) to determine optimal electrode placement using knowledge from electrode placement efficacy for other participants with similar topological brain wave activity patterns.

The AI-assisted optimum feedback modality engine 512 is responsible for automatically selecting the most optimal feedback modalities based upon an "interview" with the participant and various history and parameters. This interview involves presenting various types of feedback (such as different soundtracks and sounds to elicit certain response both positive and negative) and to measure and analyze the resultant brain activity. Depending upon the goals, the optimal feedback may be a largest value, a smallest value, or even a predetermined value. One of the outcomes of the interview process is to determine how the participant's brain individually reacts to enable the BTFS to customize the feedback for that particular user given particular objectives and to train the various machine learning computation engines that will later be used (the AI-assisted signal processing and classification engines 513) to process the signal data.

Goals of this interview process include determining the following:
which sounds does this brain like for each frequency band (e.g., which sounds produce the highest amplitude and synchrony for each band);
which sounds does this brain dislike;
which sounds make this brain the most predictable (e.g., how well can the machine learning algorithms determine where a received data stream is likely to move next)
what the data looks like when the brain deliberately tries to suppress particular frequencies, and can it determine a reliable trigger model (to elicit the suppression or evocation)
what the data looks like when the brain is producing a spindle of brain waves in each frequency and can it determine an accurate model for the brain of this participant for detecting an entrance to a spindle.

These goals are achieved by playing particular soundtracks in combination with audible commands to cause the participant to recall various kind of emotion evoking memories (e.g., happy, sad, loving, angry, etc. memories). Details of these interview techniques are described further below with reference to FIGS. 13A-13B.

The AI-assisted signal processing and classification engines 513 provide the machine learning modules (algorithms and trained model instances) for processing the raw digital signal data received from the amplifier (e.g., amplifier output from amplifier 110 of FIG. 1 via communication path 111 or from the BWPMS 120). As briefly explained, one of the outcomes of the interview process performed by the AI-assisted optimum feedback modality engine 512 is determining the best performing machine learning models for the particular participant based upon real measurement of data. In one example AI-based BTFS, five separate machine learning models are used to process each channel for a participant, two models of which have been individually optimized for the participant. (So, for example, in a four-channel system, there are five machine learning models for each of the four channels, twenty in total.) In some example BTFSes, the models are long short-term memory (LSTM) recurrent neural network (RNN) engines. In one such environment, open source libraries and tools for GOOGLE's TENSORFLOW are utilized. Other libraries, packages, languages, RNN and LSTM implementations may be similarly incorporated. In addition, other example BTFS implementations incorporate different numbers of models and different types of models, as well as possibly mixing types of models (some LSTM based RNN and others) to implement a different type of ensemble voting. A further discussion of the inputs and outputs to a typical AI-assisted signal processing and classification engine 513 is described below with reference to FIG. 12.

The AI-assisted adaptive feedback generation component 515 customizes and adapts the feedback generation for the participant over time as the participant becomes better (or worse) at brain training. In addition, in some example BTFSes, the AI models used for signal processing and classification can be trained to automatically and dynamically identify certain types of events (triggers) such as when signal patterns are about to rise or fall and, in response, cause an intervention to facilitate "boosting" the participant brain into a desired state. For example, if patterns are recognized for the participant that show that the participant is about to fall asleep or lose concentration while training for alpha wave performance, the BTFS can automatically cause special feedback to try to get the participant back on track, for example, a burst of sound, flash of light, electromagnetic stimulation, or transcranial direct current stimulation (tDCS). This helps the participant "pull-up" or "push-down" brain activity similar to how a person can innervate and relax muscles and is termed "Keep Me In." Example algorithms and techniques for adapting feedback generation are described further with respect to Figures C and D below.

To begin a typical BTFS brain training session, a participant enters a darkened room, a "pod" (not shown), which implements a controlled environment, the size of a small sitting area, for the duration of the session. In BTFS examples, the pod includes a comfortable place to sit and wear the electrodes (e.g., a reclining chair), and potentially presentation or feedback devices such as a display screen and surround sound speakers. Lighting and sound are both controlled and can be customized for the participant.

FIGS. 6-9C are example screen displays from an example Brain Training Feedback System environment using one or more example Brain Wave Processing and Monitoring Systems and/or example AI-Assisted Brain Wave Processing and Monitoring Engines. Other BTFS examples may have other display screens, in other orders, and with other content.

Figure 6:
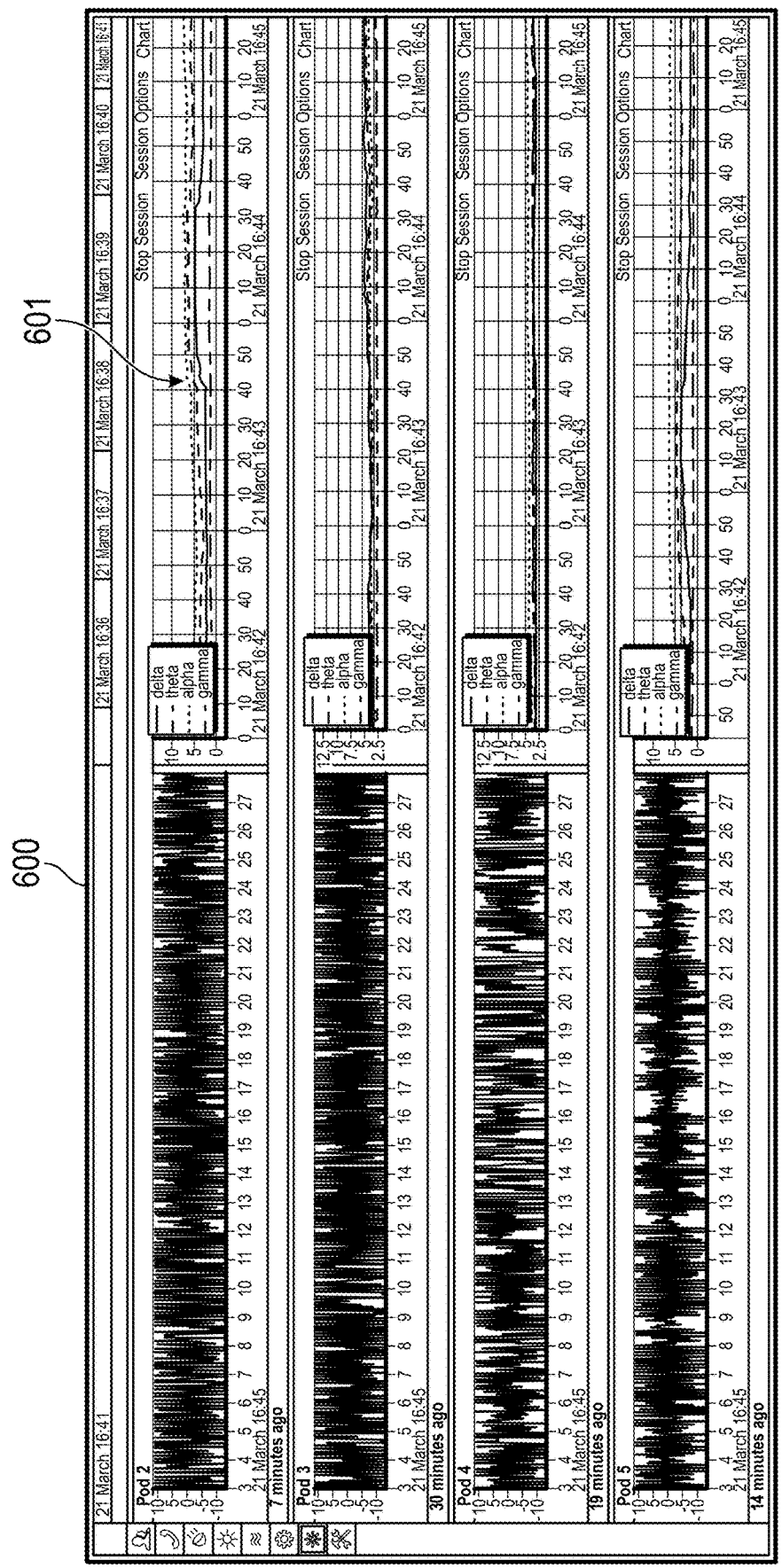
FIGS. 6, 7A-7B, 8, and 9A-9D are example screen displays from an example Brain Training Feedback System environment using one or more example Brain Wave Processing and Monitoring Systems and/or example AI-Assisted Brain Wave Processing and Monitoring Engines.

FIG. 6 is an example screen display of electronic output corresponding to four different example Brain Training Feedback System pods. The output is a summary session control panel displayed to monitor the ongoing sessions, for example by the administrator 140 in FIG. 1. The summary screen 600 represents for each pod a running average of the processed signal data on all "n" (e.g., four) channels of a participant over the entire session. For example, sub-region 601 shows a running average of the four channels of waves for the participant in "Pod 2" over the entire session.

Figure 7A:
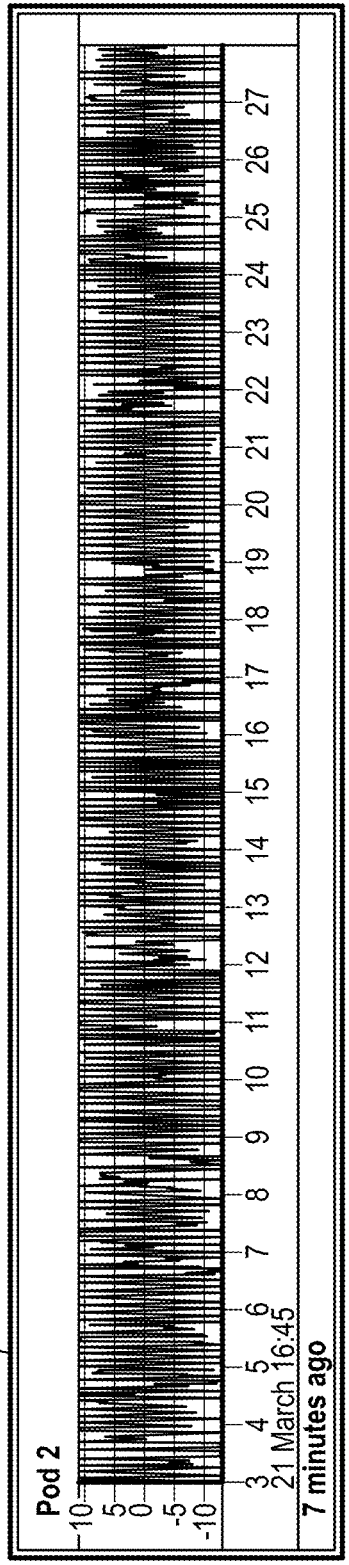
Figure 7B:
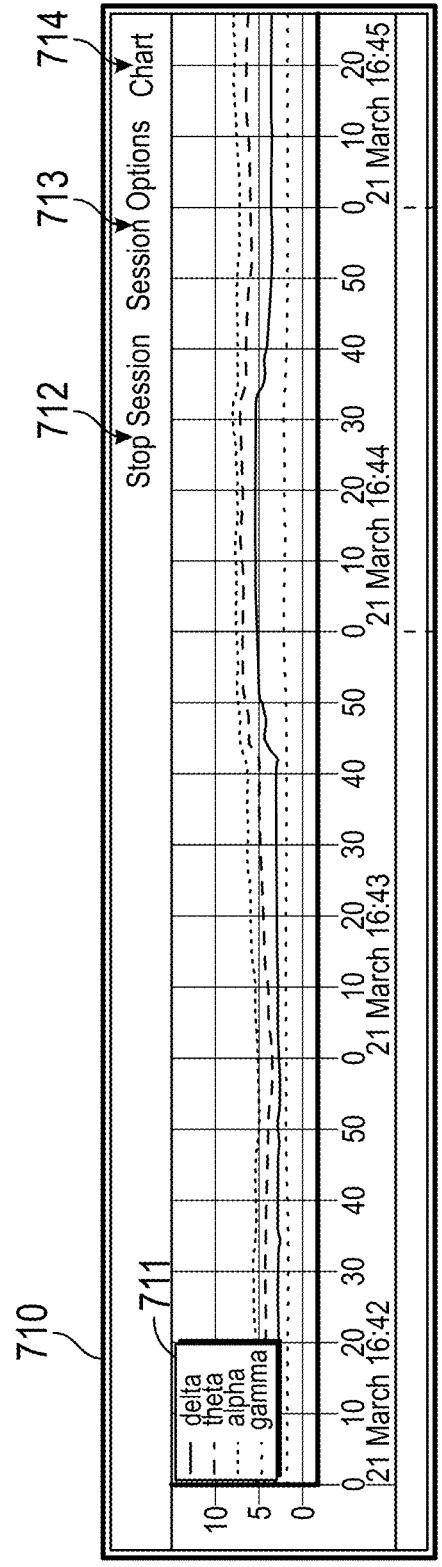

FIGS. 7A and 7B are an example screen display of a portion of FIG. 6 illustrating details of one of the electronic output from one of the pods. In particular, this is a detailed view of the output 601 for Pod 2 shown in FIG. 6. Sub-region 700 (left side of output 601) shows a running average of all four channels of processed signal data for the participant in Pod 2 over time for each second (x-axis) and the average amplitude, normalized to center on zero (y-axis). Sub-region 710 (right side of output 601) shows a distinct chart for each type of signal being measured (which may or may not be what is being trained). As observable from key 711 and the lines looking from topmost to bottom-most in a minute time-period 715, an average (running average) alpha signal is shown in blue; an average theta signal is shown in brown; an average delta signal is shown in purple; and an average gamma signal is shown in green. Selection of the UI control 712 (e.g., link labeled "Stop Session") allows the administrator to stop and start a session in the viewed pod (e.g., pod 2 in FIG. 6). Section of the UI control 714 (e.g., link labeled "Chart") allows the administrator to navigated to FIG. 8 described below. Selection of the UI control 713 (e.g., link labeled "Session Options") allows the administrator to navigate to FIG. 9A described below.

Figure 8:
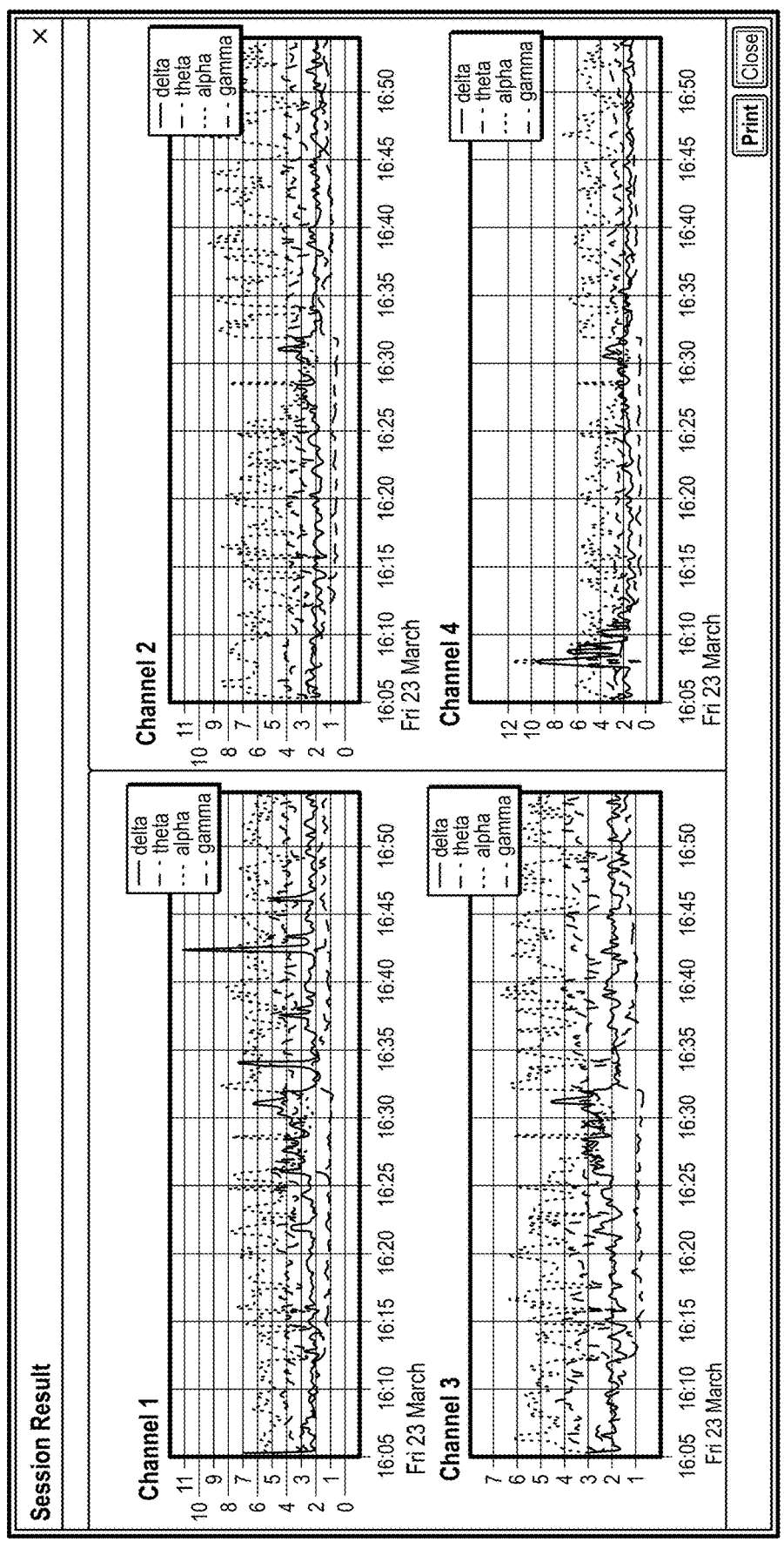

When the administrator selects UI control 714 (e.g., link labeled "Chart"), the BTFS navigates to displaying a chart for each individual channel of the participant of the corresponding pod. FIG. 8 is an example screen display of electronic brain wave output charts from different channels from one of the pods. For example, the charts shown in FIG.

8 correspond to each of the four channels for the participant of pod 2 shown in FIG. 6 in sub-region 601, when the UI control 714 is selected in that sub-region. Each of the signals being measured (here alpha, theta, delta, gamma) is displayed for each channel according to the colors shown in the key 711. Other colors, other or some of the signals could also be shown as well as other variations. As observable from these charts, the alpha activity for this participant is pronounced and likely what is being trained in this example.

When the administrator selects UI control 713 (e.g., link labeled "Session Options") the BTFS shows a (pop-up) control window for setting various controls and navigating to spectral displays of brain wave activity from channels of a particular pod. A detailed view of this control window is described below with reference to FIG. 9C. Selection of the gear icon (icon 916) allows navigation to the configuration screen for the current pod (pod 601).

FIGS. 9A-9D are example screen displays for setting session configuration and showing spectral displays of brain wave activity from channels of a particular pod. The configuration screens allow the administrator to tune the currently displayed neurofeedback session on-the-fly (dynamically) while the session is underway. The session control panel 903 is shown in the upper left corner of display 901. The icons 904 are the same controls as those shown in the pop-up control window (not shown) when control 713 is selected from sub-region 601 in FIG. 6. Two UI Controls 905 to start the session and perform an impedance test are also available.

For example, the screen display 901 shown in FIG. 9A displays spectral charts of brain wave activity 910 from each of the four channels for the participant of pod 2. An annotated view of display 910 is shown in FIG. 9B. Each spectral chart is a continuous display over time (z-axis) of the brain wave activity (all frequencies from 1 Hz-44 Hz, from right to left (x-axis). The peaks correspond to amplitude in microvolts (y-axis). The landscape scrolls away from the viewer so that the most recent reading appears in front and the entire graph displays about 30 seconds of activity. The flatter blue areas are wave frequencies that the participant is not currently producing. Peaked green (progressing to yellow, then red for higher amplitudes) show wave frequencies being produced at higher amplitude levels. In the illustrated example, the participant is generating a peak along the 10 Hz on channel 1 and producing less on channel 2 but is still producing some activity. On channel 3, the participant is producing very high activity (high amplitude) over a wider spread of frequencies (7-12 Hz). On channel 4, the participant is producing waves of similar frequencies to channel 3, but weaker signals.

Figure 9C:
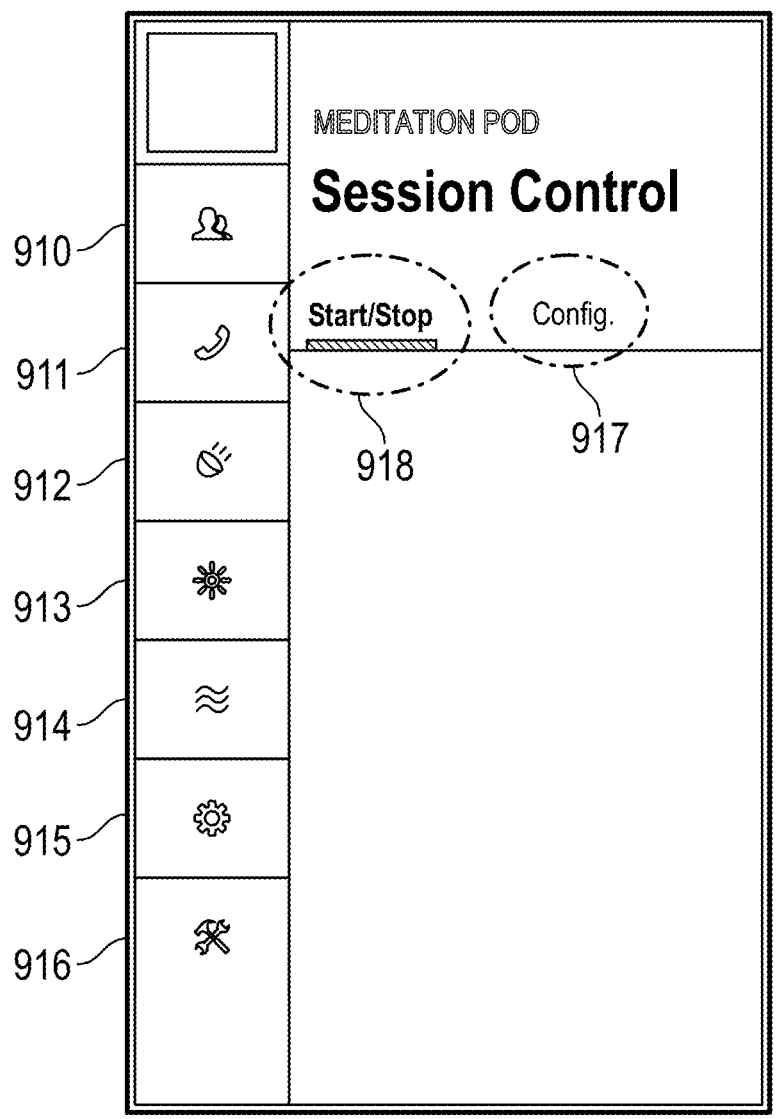

The session control panel 903 shown in the upper left corner of display 901 allows the administrator to control the current session being displayed. FIG. 9C is a detailed view of session control panel 903. The UI control 917 (labeled "Config") allows navigation to options for controlling the parameters of the session. An example display for controlling parameters is described below with reference to FIG. 9D. The UI control 918 (labeled "Start/Stop") allows the administrator to stop and start the current session. The UI controls on the left hand side of the session control panel 901 include people icon 910 for choosing the participant and account management; phone icon 911 for engaging in a communication session with the participant (the participant can contact the administrator for help or advice during the session from the pod); speaker icon 912 for adjust sound in the pod; light icon 913 for adjusting color of the LED lighting inside of the pod; waves icon 914 for toggling a real-time feedback display for the participant in the pod (which could contain instructions, spectral activity, or other content); gear icon 915 for navigating to the session configuration displays (FIG. 9A); and hammer/screwdriver icon 916 for navigating to the summary session control panel (FIG. 6).

Figure 9D:
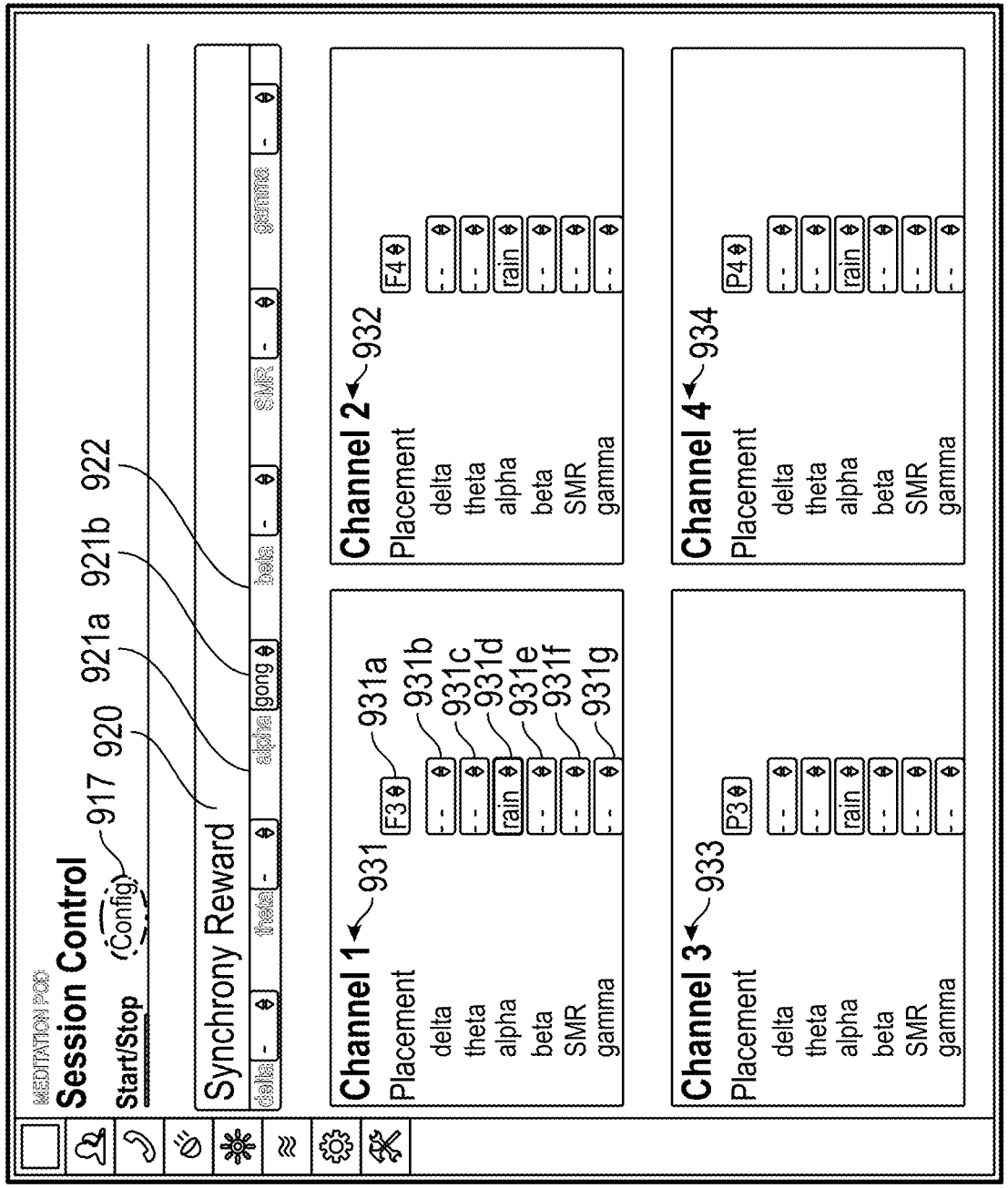

FIG. 9D is an example screen display enabling parameter set up for the current session of the participant being administered. This screen may be displayed, for example, as part of the logic for block 302 in FIG. 3. From this display, an administrator can set parameters for synchrony rewards as well as for specific brain wave rewards. For example, control area 920 is used to set the rewards for synchrony of one or more brain wave types. For example, UI control 921a and 922 allow setting rewards for alpha and beta waves, respectively. Each of the menus for setting synchrony awards, for example, UI control (menu) 921b (not shown), allows selection of a sound for example, a gong, bell, high chime, low chime, "ohm" (chanting sound), cello (continuous reward), or none. Control areas 931-934 allow the administrator to indicate electrode placement and the reward for each brain wave type for each of channels 1-4, respectively. For example, the placement menu 931a for setting electrode placement for channel 1 allows the administrator to select from all 10-20 electrode placement locations. Each frequency reward menu, for example, menus 931b-g, allows selection a sound from a menu including rain, thunder, creek, wind, space, cello, violin, choir, bells, or none. The BTFS can be easily customized to add more and/or different sounds to any of these menus. In addition, other user interface controls and displays can be similarly incorporated for an example BTFS.

Example embodiments described herein provide applications, tools, data structures and other support to implement a Brain Training Feedback System to be used for training a participant's brain to evoke/increase or suppress/inhibit certain brain wave activity based upon the desired task at hand. Other embodiments of the described techniques may be used for other purposes, including for other non-medical and for medical uses. In the following description, numerous specific details are set forth, such as data formats and code sequences, etc., in order to provide a thorough understanding of the described techniques. The embodiments described also can be practiced without some of the specific details described herein, or with other specific details, such as changes with respect to the ordering of the logic, different logic, etc. Thus, the scope of the techniques and/or functions described are not limited by the particular order, selection, or decomposition of aspects described with reference to any particular routine, module, component, and the like.

Also, although certain terms are used primarily herein, other terms could be used interchangeably to yield equivalent embodiments and examples. In addition, terms may have alternate spellings which may or may not be explicitly mentioned, and all such variations of terms are intended to be included.

Figure 10:
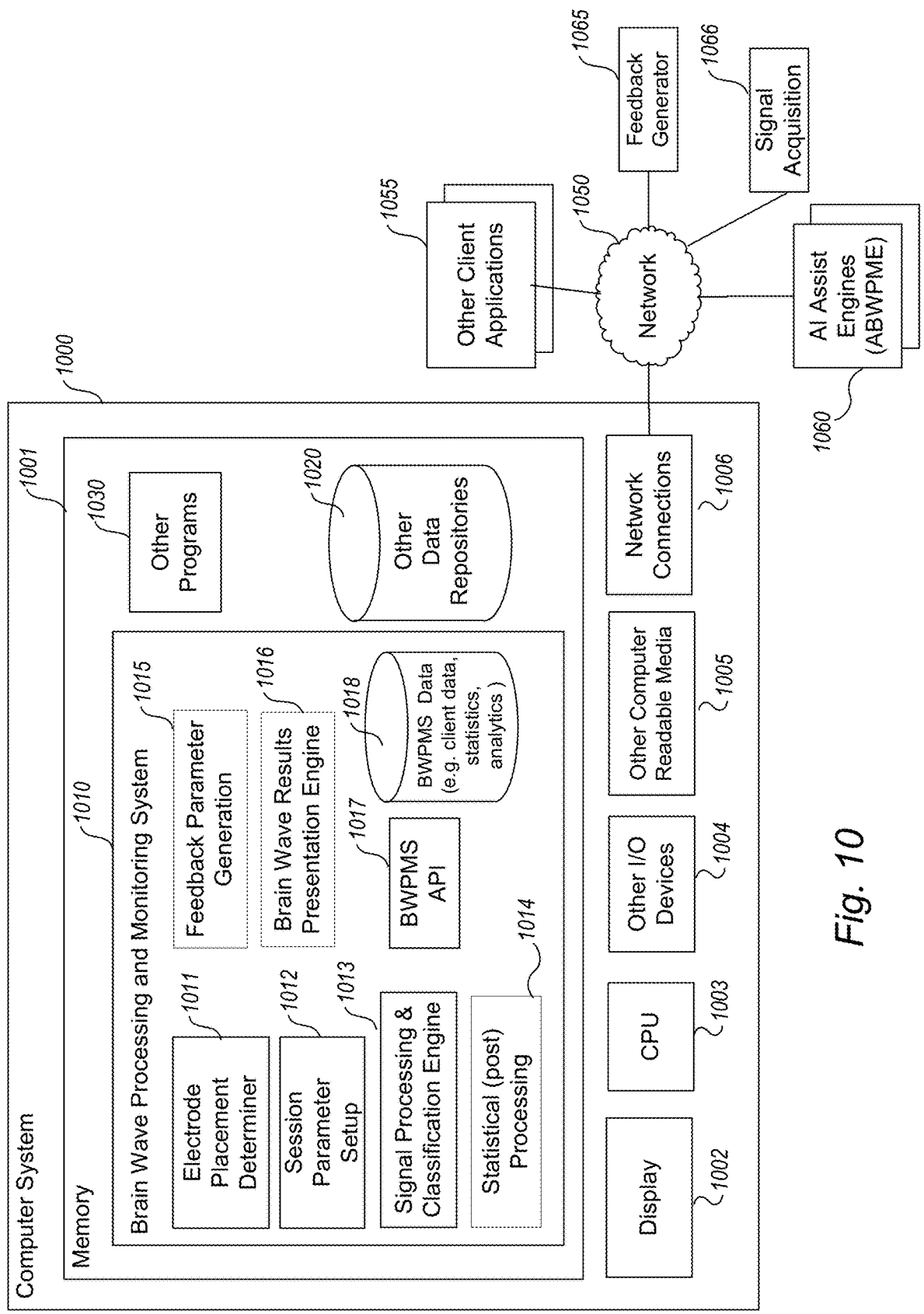
FIG. 10 is an example block diagram of a computing system for practicing embodiments of a Brain Wave Processing and Monitoring.

FIG. 10 is an example block diagram of a computing system for practicing embodiments of a Brain Wave Processing and Monitoring System. Note that one or more general purpose virtual or physical computing systems suitably instructed or a special purpose computing system may be used to implement an BWPMS. However, just because it is possible to implement the a BWPMS on a general purpose computing system does not mean that the techniques themselves or the operations required to implement the techniques are conventional or well known. Further, the BWPMS may be implemented in software, hardware, firmware, or in some combination to achieve the capabilities described herein.

The computing system 1000 may comprise one or more server and/or client computing systems and may span distributed locations. In addition, each block shown may represent one or more such blocks as appropriate to a specific embodiment or may be combined with other blocks. Moreover, the various blocks of the Brain Wave Processing and Monitoring System 1010 may physically reside on one or more machines, which use standard (e.g., TCP/IP) or proprietary interprocess communication mechanisms to communicate with each other.

In the embodiment shown, computer system 1000 comprises a computer memory ("memory") 1001, a display 1002, one or more Central Processing Units ("CPU") 1003, Input/Output devices 1004 (e.g., keyboard, mouse, CRT or LCD display, etc.), other computer-readable media 1005, and one or more network connections 1006. The BWPMS 1010 is shown residing in memory 1001. In other embodiments, some portion of the contents, some of, or all of the components of the BWPMS 1010 may be stored on and/or transmitted over the other computer-readable media 1005. The components of the BWPMS 1010 preferably execute on one or more CPUs 1003 and manage the brain training and neurofeedback, as described herein. Other code or programs 1030 and potentially other data repositories, such as data repository 1020, also reside in the memory 1001, and preferably execute on one or more CPUs 1003. Of note, one or more of the components in FIG. 10 may not be present in any specific implementation. For example, some embodiments embedded in other software may not provide means for user input or display.

In a typical embodiment, the BWPMS 1010 includes one or more electrode placement determiner 1011, one or more session parameter setup units 1012, one or more signal processing and classification engines 1013, one or more statistical processing units 1014, one or more feedback parameter generation units 1015, one or more brain wave results presentation engines 1016, and a BWMPS data repository 1018 containing e.g., the client data, statistics, analytics, etc. These components operate as described with reference to FIGS. 3 and 4. In at least some embodiments, the statistical (post) processing unit 1014 is provided external to the BWPMS and is available, potentially, over one or more networks 1050. Other and/or different modules may be implemented. In addition, the BWPMS may interact via a network 1050 with application or client code 1055 that e.g. uses results computed by the BWPMS 1010, one or more AI-Assisted Brain Wave Processing and Monitoring Engines 1060, one or more feedback generators 1065, and/or one or more third-party signal acquisition systems 1065. Also, of note, the data repository 1018 may be provided external to the BWPMS as well, for example in a knowledge base accessible over one or more networks 1050.

In an example embodiment, components/modules of the BWPMS 1010 are implemented using standard programming techniques. For example, the BWPMS 1010 may be implemented as a "native" executable running on the CPU 103, along with one or more static or dynamic libraries. In other embodiments, the BWPMS 1010 may be implemented as instructions processed by a virtual machine. A range of programming languages known in the art may be employed for implementing such example embodiments, including representative implementations of various programming language paradigms, including but not limited to, object-oriented, functional, procedural, scripting, and declarative.

The embodiments described above may also use well-known or proprietary, synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously and communicate using message passing techniques. Equivalent synchronous embodiments are also supported.

In addition, programming interfaces 1017 to the data stored as part of the BWPMS 1010 (e.g., in the data repository 1018) can be available by standard mechanisms such as through C, C++, C#, and Java APIs; libraries for accessing files, databases, or other data repositories; through scripting languages such as XML, ECMAscript, Python or Perl; or through Web servers, FTP servers, or other types of servers providing access to stored data. The data repository 1018 may be implemented as one or more database systems, file systems, or any other technique for storing such information, or any combination of the above, including implementations using distributed computing techniques.

Also, the example BWPMS 1010 may be implemented in a distributed environment comprising multiple, even heterogeneous, computer systems and networks. Different configurations and locations of programs and data are contemplated for use with techniques of described herein. In addition, the BWPMS components may be physical or virtual computing systems and may reside on the same physical system. Also, one or more of the modules may themselves be distributed, pooled or otherwise grouped, such as for load balancing, reliability or security reasons. A variety of distributed computing techniques are appropriate for implementing the components of the illustrated embodiments in a distributed manner including but not limited to TCP/IP sockets, RPC, RMI, HTTP, Web Services (Websockets, XML-RPC, JAX-RPC, SOAP, etc.) and the like. Other variations are possible. Also, other functionality could be provided by each component/module, or existing functionality could be distributed amongst the components/modules in different ways, yet still achieve the functions of an BWPMS.

Furthermore, in some embodiments, some or all of the components of the BWPMS 1010 may be implemented or provided in other manners, such as at least partially in firmware and/or hardware, including, but not limited to one or more application-specific integrated circuits (ASICs), standard integrated circuits, controllers executing appropriate instructions, and including microcontrollers and/or embedded controllers, field-programmable gate arrays (FPGAs), complex programmable logic devices (CPLDs), and the like. Some or all of the system components and/or data structures may also be stored as contents (e.g., as executable or other machine-readable software instructions or structured data) on a computer-readable medium (e.g., a hard disk; memory; network; other computer-readable medium; or other portable media article to be read by an appropriate drive or via an appropriate connection, such as a DVD or flash memory device) to enable the computer-readable medium to execute or otherwise use or provide the contents to perform at least some of the described techniques. Some or all of the components and/or data structures may be stored on tangible, non-transitory storage mediums. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

Figure 11:
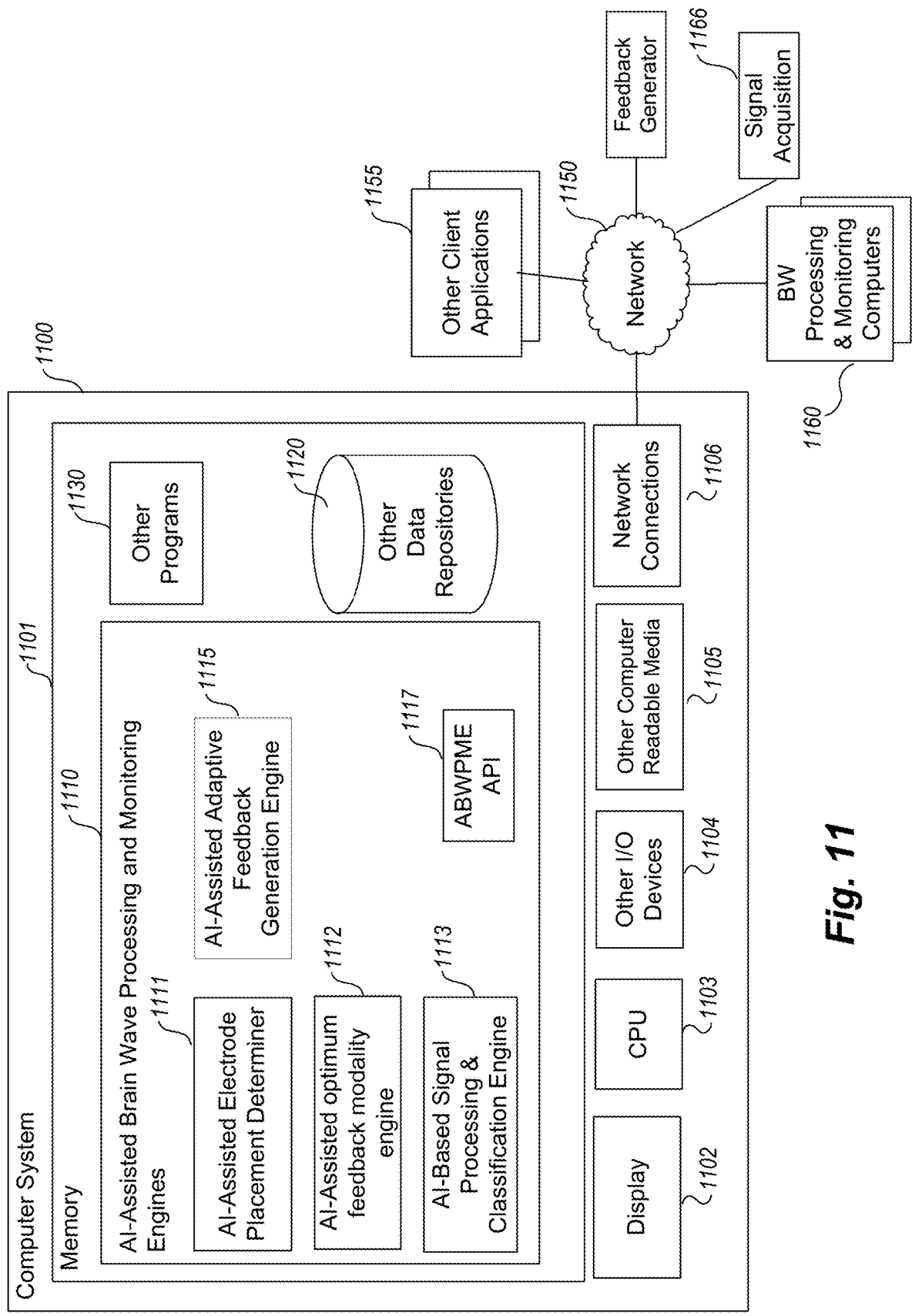
FIG. 11 is an example block diagram of a computing system for practicing embodiments of an AI-Assisted Brain Wave Processing and Monitoring Engine.

FIG. 11 is an example block diagram of a computing system for practicing embodiments of an AI-Assisted Brain Wave Processing and Monitoring Engine. Note that one or more general purpose virtual or physical computing systems suitably instructed or a special purpose computing system may be used to implement an ABWPME. However, just because it is possible to implement the a ABWPME on a general purpose computing system does not mean that the techniques themselves or the operations required to implement the techniques are conventional or well known. Further, the ABWPME may be implemented in software, hardware, firmware, or in some combination to achieve the capabilities described herein.

The computing system 1100 may comprise one or more server computing systems or servers on one or more computing systems and may span distributed locations. In addition, each block shown may represent one or more such blocks as appropriate to a specific embodiment or may be combined with other blocks. Moreover, the various blocks of the AI-Assisted Brain Wave Processing and Monitoring Engines 1010 may physically reside on one or more machines, which use standard (e.g., TCP/IP) or proprietary interprocess communication mechanisms to communicate with each other and with other parts of the system In the embodiment shown, computer system 1100 comprises a computer memory ("memory") 1101, a display 1102, one or more Central Processing Units ("CPU") 1103, Input/Output devices 1104 (e.g., keyboard, mouse, CRT or LCD display, etc.), other computer-readable media 1105, and one or more network connections 1106. These components operate similarly to those mentioned above with respect to FIG. 10. The ABWPMEs 1110 are shown residing in memory 1101. The components of the ABWPMEs 1110 preferably execute on one or more CPUs 1103 and manage the brain training and neurofeedback, as described herein. In a typical embodiment, the ABWPMEs 1010 includes one or more AI-assisted electrode placement determiners 1111, one or more AI-assisted optimum feedback modality engines 1112, one or more AI-based signal processing and classification engines 1113, and one or more AI-assisted adaptive feedback generation engines. These components operate as described with reference to FIGS. 3 and 5.

Of note, one or more of the components in FIG. 11 may not be present in any specific implementation. In addition, the various configurations and options described with reference to FIG. 10 may be used to implement the components of the ABWPMEs 1110 and the components of computer system 1100. As explained above with reference to FIG. 5, the ABWPMEs may operate as servers in conjunction with the rest of the components of a BTFS to implement a neurofeedback system.

As described with respect to FIGS. 1, 3, and 5, one form of an example BTFS (e.g., BTFS 102) incorporates machine learning and artificial intelligence techniques to deconstruct and analyze or classify received EEG signals (brain activity) from a participant via an amplifier and to cause feedback to the participant via a feedback generator.

Figure 12:
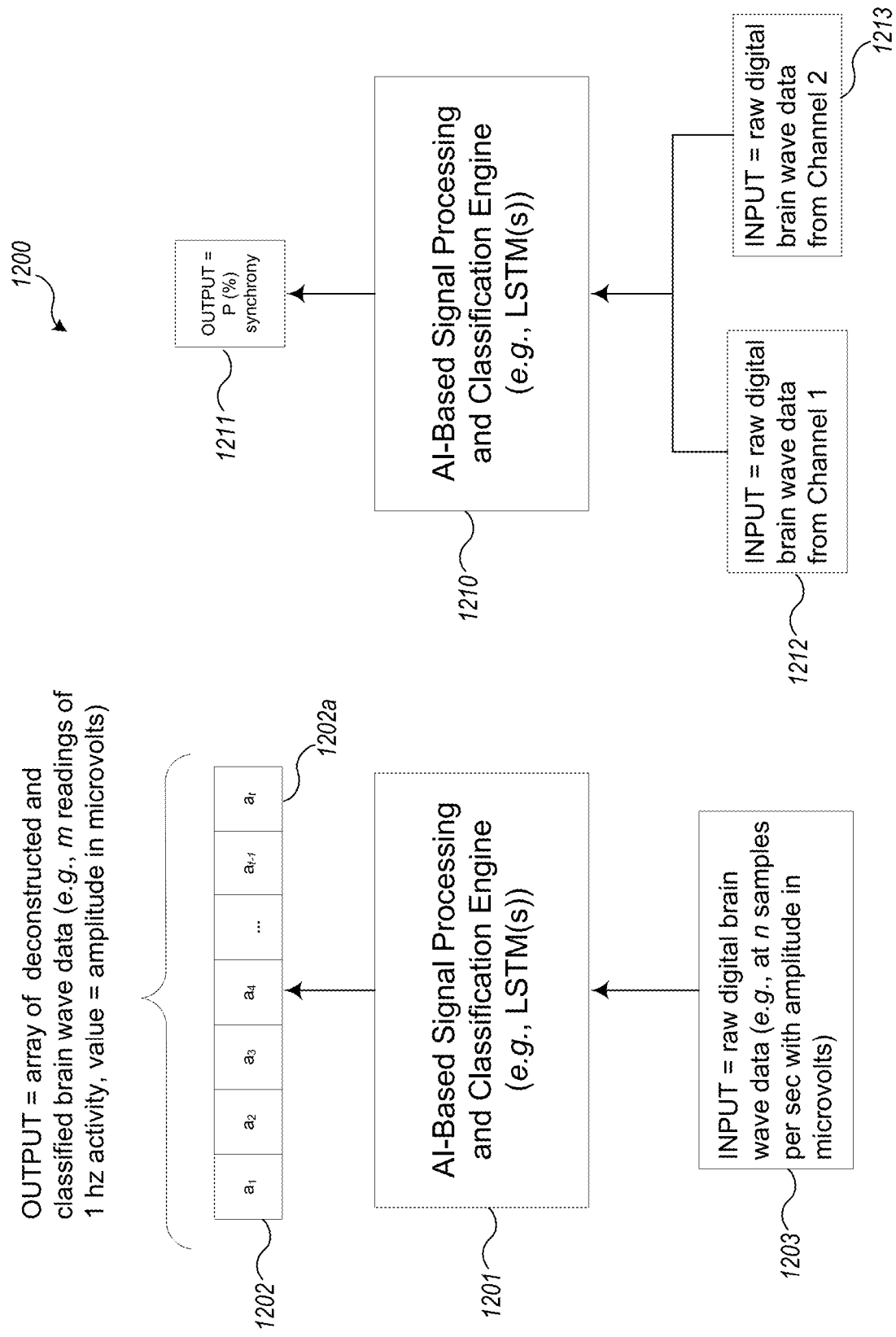
FIG. 12 is an example block diagram of inputs and outputs provided to an example AI-Assisted Brain Wave Processing and Monitoring Engine (machine learning computation engine) to perform signal processing and classification of detected brain wave signals.

FIG. 12 is an example block diagram of inputs and outputs provided to an example AI-Assisted Brain Wave Processing and Monitoring Engine (machine learning computation engine) to perform signal processing and classification of detected brain wave signals. An example ABWPME uses an LSTM recurrent neural network to implement machine learning, although as mentioned other machine learning modules could be incorporated as well or instead of these. In one such example, the LSTM engines are defined using open source libraries and tools for GOOGLE's TENSORFLOW. Other libraries, packages, languages, RNN and LSTM implementations may be similarly incorporated.

FIG. 12 describes the inputs and outputs to an ABWPME in two scenarios 1200. The two models ABWPME 1201 and 1210 are shown as "black boxes" because they are defined and implemented by the third-party libraries of TENSORFLOW. Other libraries similarly incorporated may be used by defining inputs and outputs similar to those shown in FIG. 12.

In one model, the ABWPME 1201 is used for training for a particular brain wave frequency and consists of one input 1203 and an output array 1202. The input 1203 is "raw" digital brain wave data at a particular sampling rate with values comprising, for example, amplitude expressed in microvolts. The output array 1202 comprises an array of deconstructed and classified brain wave data (processed signal data), for example, "m" readings of 1 Hz activity, where each value is an amplitude expressed in microvolts.

In the other model, the ABWPME 1210 is used for synchrony training and consists of two inputs 1212 and 1213 and an output 1211, which value represents a percentage of synchrony achieved. This value could be a number or other discrete value expressing percentage or quality of synchrony achieved. Inputs 1212 and 1213 contain "raw" digital brain wave data from two different channels, respectively, at a particular sampling rate with values comprising, for example, amplitude expressed in microvolts.

The LSTMs 1201 and 1210 are capable of operating on raw data received on a sequential basis (because of the use of neural networks). Accordingly, the processed signal data output by the models in the ABWPMEs 1200 generate processed signal data without using FFTs or other methods requiring large amounts of sample data.

FIGS. 13A through 15 illustrate example logic for the components of an ABWPME as described in FIGS. 5 and 11 using the models described with reference to FIG. 12.

Figure 13A:
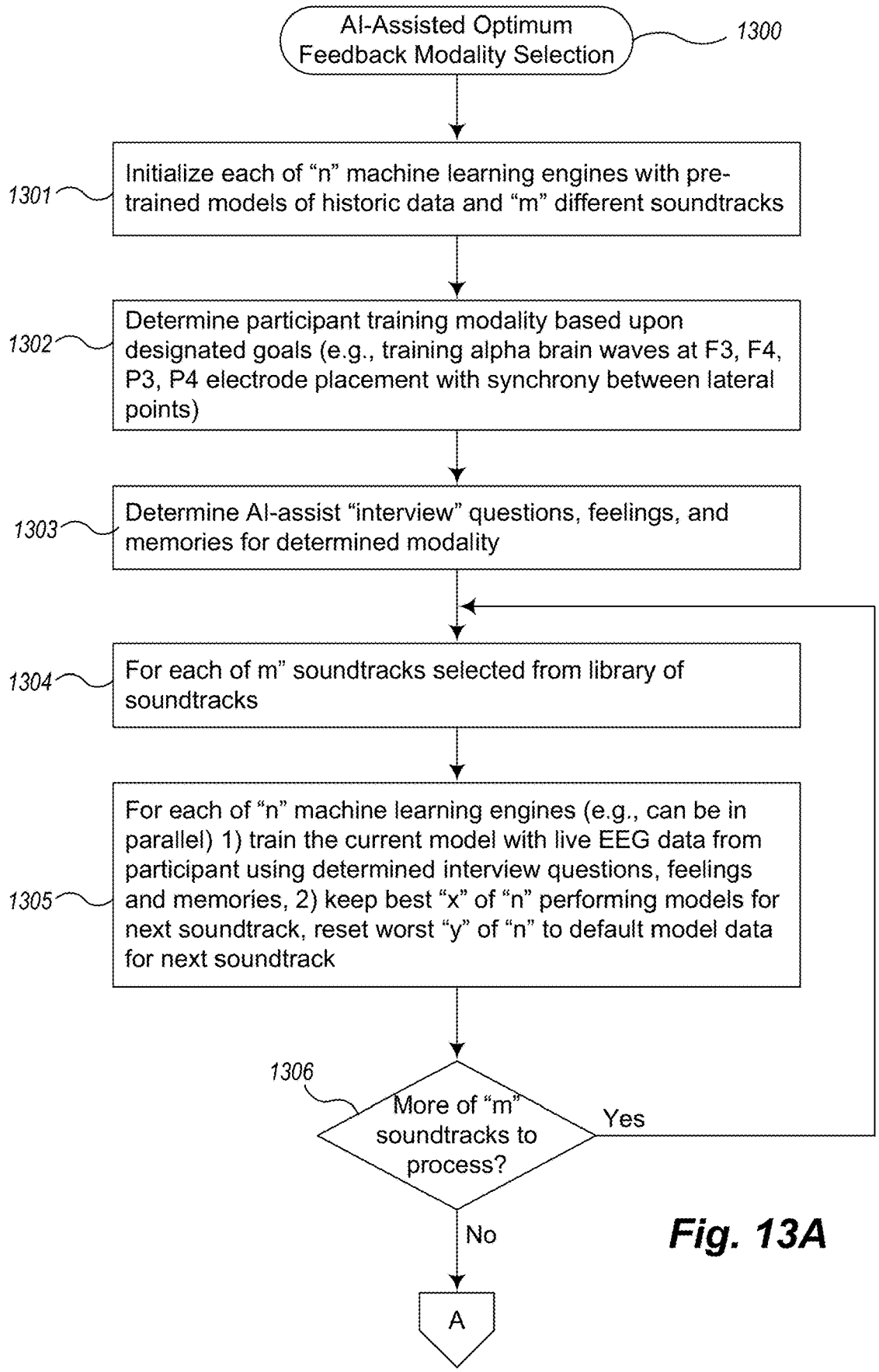
FIGS. 13A-13B are an example flow diagram of code logic provided by an example AI-Assisted Brain Wave Processing and Monitoring Engine to set optimal feedback modalities.
Figure 13B:
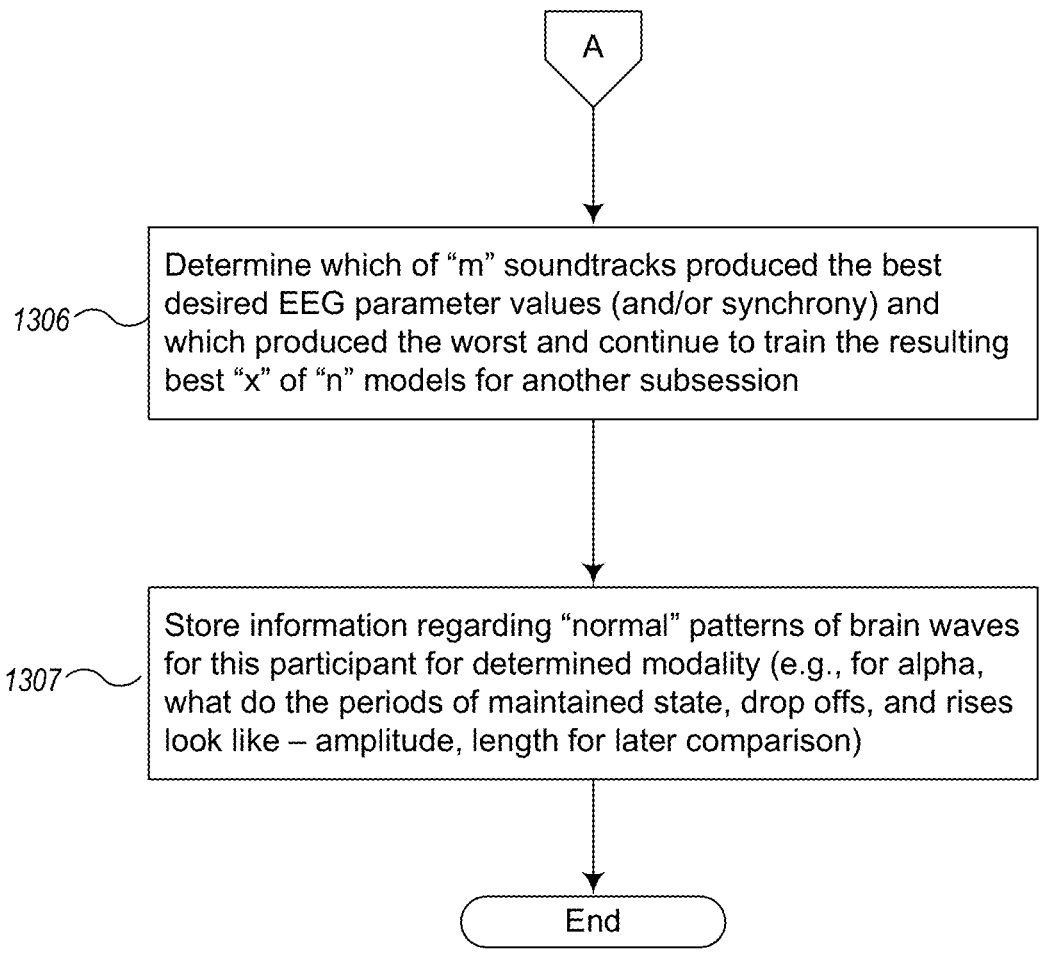

FIGS. 13A-13B are an example flow diagram of code logic provided by an example AI-Assisted Brain Wave Processing and Monitoring Engine to set optimal feedback modalities. In an example BTFS, logic 1300 can be performed by the AI-assisted optimum feedback modality engine 512 of FIG. 5 or the engine 1112 of FIG. 11. The logic 1300 is responsible for initial selecting of a customized brain training feedback and reward structure for a particular participant.

Specifically, in block 1301, the logic initializes each of some number of machine learning models (engines) with pre-trained models based upon historic participant data and with some number of different soundtracks. In one example ABWPME, five machine learning models are employed for each brain wave frequency (or synchrony) being trained. Other BTFS examples may use a different number of models and may employ ensemble voting techniques to derive answers.

In block 1302, the logic determines (which may be selected or pre-designated) which modality is being trained based upon indicated goals, electrode placements, etc.

In block 1303, the logic determines through the AI-assisted interview process characteristics of and a "factorization" for the participant. Each participant can then be described as a vector of parameters which characterize the participant's learning capabilities and behaviors. As mentioned above with respect to FIG. 5, an ABWPME (e.g., AI-assisted optimum feedback modality engine 512) is responsible for automatically selecting the most optimal feedback modalities based upon an "interview" with the participant and various history and parameters. The interview process is used to determine:

- which sounds does this brain like for each frequency band (e.g., which sounds produce the highest amplitude and synchrony for each band);
- which sounds does this brain dislike;
- which sounds make this brain the most predictable (e.g., how well can the machine learning algorithms determine where a received data stream is likely to move next)
- what the data looks like when the brain deliberately tries to suppress particular frequencies, and can it determine a reliable trigger model (to elicit the suppression or evocation)
- what the data looks like when the brain is producing a spindle of brain waves in each frequency and can it determine an accurate model for the brain of this participant for detecting an entrance to a spindle.

A spindle is a discrete and bounded burst of neural activity in a measured frequency. Automatic spindle detection is a unique capability of BTFS examples described herein and is made possible by use of the ABWPMEs which can learn what a spindle looks like for a particular frequency for that participant. This knowledge (machine learning) can be used to predict interventions as described below with respect to FIGS. 14 and 15 when the BTFS detects that a participant is about to lose a spindle-rich phase, thereby increasing efficacy and efficiency of brain training techniques. For example, this data can be uses to detect when the participant's brain is performing exercises so that the soundtrack can be modified to assist (see FIGS. 14 and 15).

As mentioned, these goals are achieved by playing particular soundtracks in combination with audible commands to cause the participant to recall various kind of emotion evoking memories (e.g., happy, sad, loving, angry, etc. memories). In blocks 1304-1306, the logic determines and records information for each of the soundtracks and uses this information to determine some number "x" (e.g., two) of best performing participant trained models to integrate with the pre-trained models for actual brain feedback training. Specifically, in block 1304, for each of the total number of soundtracks being tested, the logic performs a loop in block 1305 for each machine learning model to 1) train the model with live EEG data from the participant responsive to the interview (e.g., questions, tested soundtracks and sounds, feelings, and memories) and 2) select the best "x" number of five (or "n") performing models for the testing the next soundtrack and reset the remaining worst of five models for testing the next soundtrack in the loop. In block 1306, the logic determines whether there are any more soundtracks to test and, if so, returns to the beginning of the loop in block 1304, otherwise continues to block 1307.

In block 1307, the logic determines which of the tested number "m" of soundtracks produced the best desired EEG parameter values and/or synchrony percentages and which produced the worst and continues to train the selected best "x" (e.g., two) performing models in preparation for the upcoming sub-session (if a session was paused) or session.

In block 1308, the logic stores information/data regarding the "normal" patterns of brain waves for this participant for the selected modality (the characteristics or factorization) for future use. The information indicates the parameters for the brain wave signal patterns (e.g., amplitude and duration) for that individual for periods of maintained state, drop offs, and rises, which can be used for later comparisons. The logic then ends.

Figure 14:
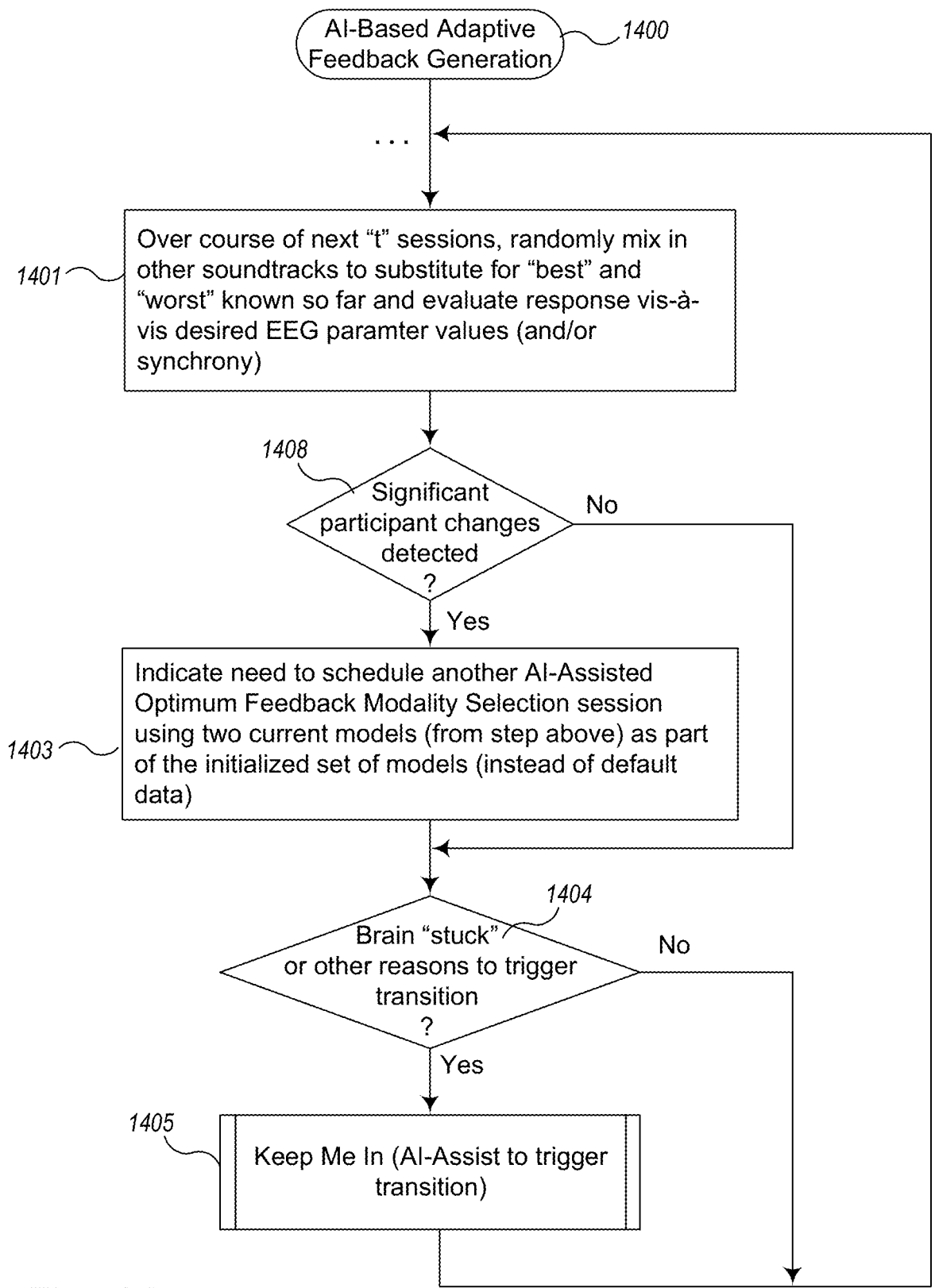
FIG. 14 is an example flow diagram of code logic provided by an example AI-Assisted Brain Wave Processing and Monitoring Engine perform adaptive feedback generation during a session.

FIG. 14 is an example flow diagram of code logic provided by an example AI-Assisted Brain Wave Processing and Monitoring Engine perform adaptive feedback generation during a session. In an example BTFS, logic 1400 can be performed by the AI-assisted adaptive feedback generation engine 515 of FIG. 5 or the engine 1115 of FIG. 11. The logic 1400 is responsible for adapting and/or customizing the rewards and/or feedback for a particular participant during a session so that the rewards/feedback adapts as the participant trains over time (hopefully to become "better" at producing desired results but could also be "worse").

In one example BTFS, the logic of blocks 1401-1405 is performed in a loop to provide continuous adaptive feedback generation. In other examples, the logic may be performed at other times, scheduled times, or responsive to other inputs.

Specifically, in block 1401, over the course of the next selected number of sessions, the ABWPME logic randomly mixes in other soundtracks (that have not yet been selected as optimal, for example, through initial screening or subsequent testing) to evaluate whether other soundtracks should be substituting as the best and worst performing.

In block 1402, the logic determines whether significant changes in the participant responses are detected and, if so, continues in block 1403, otherwise continues in block 1404.

In block 1403, the logic determines and indicates based upon what changes occurred and their significance whether to schedule another optimum feedback modality selection (interview) session using the two best current models (just found) instead of the default data.

In block 1404, the logic determines whether this participant's brain is "stuck" in its training or some other reason to trigger a transition within the training process. If so, then the logic continues to block 1405 to modify the soundtrack dynamically to assist in the triggered transition as appropriate (executes "Keep Me In" techniques), or if not, continues to block 1401 to perform continuous adaptive feedback generation.

For example, the data accumulated as a result of the interview process of Figures AA-AB can be used to detect when the participant's brain is on the brink of exiting a state, in the process of transitioning into a different state, about to create a spindle that should be rewarded, or about to drop from a spindle. In addition, if a brain has stayed in a particular state too long (for example, too long re-experiencing negative emotion or trauma, the brain may become "stuck" (for example, detected through suppression of alpha state) and the BTFS used to trigger a transition to a more positive flow state. Also, detection that the participant is falling asleep can be used to trigger a noise to keep the participant awake.

More specifically, the interview process is used to determine the characteristics of this participant's brain at the different frequencies (brain states). For example, alpha training typically produces a distinctive pattern of:

(1) High alpha amplitude; then (2) A precipitous drop in alpha amplitude; then
(3) A short period of very low alpha (30-60 seconds); then
(4) A medium spike in alpha amplitude; then
(5) A moderately fast rise in alpha amplitude; then
(6) A longer period of time in high alpha amplitude state (variable duration); then a transition back to the beginning of the pattern (1).

If the participant's brain deviates from this pattern (particularized to the individual), then the ABWPME can use this data to determine that the participant's brain is stuck. Other brain wave frequencies produce other patterns.

Figure 15:
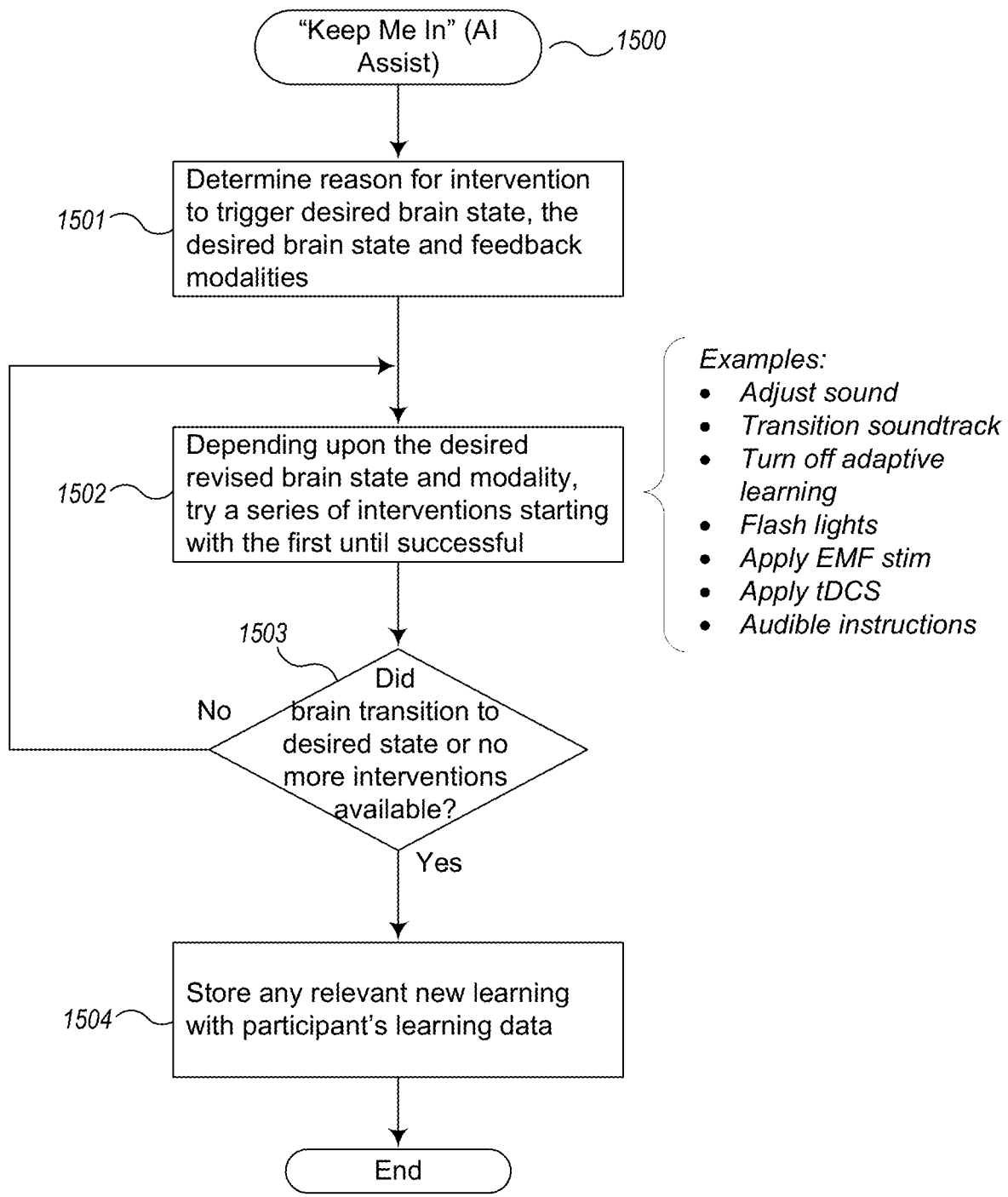
FIG. 15 is an example flow diagram of code logic provided by example AI-assisted adaptive feedback generation code logic to trigger desired brain state.

FIG. 15 is an example flow diagram of code logic provided by example AI-assisted adaptive feedback generation code logic to trigger desired brain state. For example, as described with respect to FIG. 14, when the ABWPME detects certain conditions in block 1404, the logic of FIG. 15 can be invoked to trigger a transition of the participant's brain into a desired state.

Specifically, in block 1501, the logic determines the reason for the intervention needed and a desired brain state and feedback modalities. Then, in blocks 1502-1503, the logic tries a series of interventions until the participant transitions to the desired brain state. In particular, in block 1502, the ABWPME may try one or more of: adjusting the sound, transitioning the soundtrack, turning off adaptive feedback, flashing lights, applying electromagnetic stimulation, applying tDCS, audible instructions, visual cues, or other interventions to attempt to trigger the transition to the desired state. In block 1503, the logic determines whether the brain has transitioned to the desired state or whether it has exhausted all interventions possible and, if so, continues in block 1504, otherwise continues back to try the next intervention in block 1502.

In block 1504, the logic stores any relevant new data learned during these interventions, for example, whether other soundtracks performed better or what stimulations were effect to transition the participant to the desired state. The logic then ends.

From the foregoing it will be appreciated that, although specific embodiments have been described herein for purposes of illustration, various modifications may be made without deviating from the spirit and scope of the invention. For example, the methods, systems, and techniques for performing brain feedback training discussed herein are applicable to other architectures other than a client-server architecture. Also, the methods and systems discussed herein are applicable to differing protocols, communication media (optical, wireless, cable, etc.) and devices (such as wireless handsets, electronic organizers, personal digital assistants, portable email machines, game machines, pagers, navigation devices such as GPS receivers, etc.).

The invention claimed is:

1. A neurofeedback system comprising:
a memory device configured to store an EEG signal generated by an electrode placed on an exterior of a head of a user to measure an activity of a brain of the user;
a network interface configured to receive a plurality of instructions from an electronic device via a computer network; and
one or more processors in communication with the memory device and the network interface, the one or more processors being configured to:
filter the EEG signal to generate a plurality of filtered signals including a first filtered signal and a second filtered signal, the first filtered signal having a first frequency range within a first frequency band and the second filtered signal having a second frequency range within a second frequency band different from the first frequency band, the first filtered signal corresponding to a first type of brain wave and the second filtered signal corresponding to a second type of brain wave different from the first type of brain wave;
determine from the plurality of instructions to monitor whether a first amplitude associated with the first filtered signal satisfies a first threshold;
generate a first feedback for presentation to the user in response to a determination that the first amplitude associated with the first filtered signal satisfies the first threshold;
determine from the plurality of instructions to monitor whether a second amplitude associated with the second filtered signal satisfies a second threshold; and
generate a second feedback for presentation to the user in response to a determination that the second amplitude associated with the second filtered signal satisfies the second threshold, the second feedback being different from the first feedback.

2. The neurofeedback system of claim 1, wherein the plurality of instructions indicates to monitor the first type of brain wave and the second type of brain wave.

3. The neurofeedback system of claim 1, wherein the one or more processors are configured to determine from the plurality of instructions to associate the first feedback with the first filtered signal so that the first feedback is generated for presentation to the user in response to the determination that the first amplitude associated with the first filtered signal satisfies the first threshold.

4. The neurofeedback system of claim 3, wherein the first feedback comprises an audible feedback.

5. The neurofeedback system of claim 3, wherein the first feedback comprises a visual feedback.

6. The neurofeedback system of claim 3, wherein the first feedback comprises a tactile feedback.

7. The neurofeedback system of claim 1, wherein the one or more processors are configured to determine from the plurality of instructions to select one of a plurality of soundtracks to be the first feedback.

8. The neurofeedback system of claim 1, wherein the one or more processors are configured to:
determine from the plurality of instructions to associate a third feedback rather than the first feedback with the first filtered signal so that the third feedback rather than the first feedback is generated for presentation to the user in response to the determination that the first amplitude associated with the first filtered signal satisfies the first threshold; and
generate the third feedback for presentation to the user in response to the determination that the first amplitude associated with the first filtered signal satisfies the first threshold.

9. The neurofeedback system of claim 1, wherein the first type of brain wave is an alpha wave, a beta wave, a theta wave, a delta wave, or a gamma wave.

10. The neurofeedback system of claim 9, wherein the first type of brain wave is the alpha wave.

11. The neurofeedback system of claim 10, wherein the second type of brain wave is the theta wave.

12. The neurofeedback system of claim 1, wherein the one or more processors are configured to determine from the plurality of instructions to initiate processing of the EEG signal by the one or more processors.

13. The neurofeedback system of claim 1, wherein the one or more processors are configured to determine from the plurality of instructions to monitor a synchrony between the first filtered signal and another filtered signal, the another filtered signal being generated from another EEG signal that is generated by another electrode placed on the exterior of the head of the user.

14. The neurofeedback system of claim 13, wherein the one or more processors are configured to determine a value indicative of a degree of the synchrony.

15. The neurofeedback system of claim 1, wherein the first frequency band does not overlap with the second frequency band.

16. The neurofeedback system of claim 1, wherein the one or more processors are configured to determine an amplitude for presenting the first feedback from a moving average associated with the first filtered signal.

17. The neurofeedback system of claim 1, wherein the one or more processors are configured to generate the first feedback for presentation to the user in real-time with generation of the EEG signal by the electrode.

18. The neurofeedback system of claim 1, wherein the one or more processors are configured to simultaneously generate the first feedback and the second feedback for presentation to the user.

19. The neurofeedback system of claim 1, wherein the one or more processors are configured to, responsive to the plurality of instructions, transition to (i) monitoring whether the second amplitude associated with the second filtered signal satisfies the second threshold in place of (ii) monitoring whether the first amplitude associated with the first filtered signal satisfies the first threshold.

20. The neurofeedback system of claim 1, wherein the network interface is configured to communicate via the computer network according to a network protocol.

21. A method of training a user with a neurofeedback system, the method comprising:
receiving, by one or more processors, an EEG signal generated by an electrode placed on an exterior of a head of the user to measure an activity of a brain of the user;
filtering, by the one or more processors, the EEG signal to generate a plurality of filtered signals including a first filtered signal and a second filtered signal, the first filtered signal having a first frequency range within a first frequency band and the second filtered signal having a second frequency range within a second frequency band different from the first frequency band, the first filtered signal corresponding to a first type of brain wave and the second filtered signal corresponding to a second type of brain wave different from the first type of brain wave;
receiving, by a network interface, a plurality of instructions from an electronic device via a computer network;
determining, by the one or more processors, from the plurality of instructions to monitor whether a first amplitude associated with the first filtered signal satisfies a first threshold;
determining, by the one or more processors, that the first amplitude associated with the first filtered signal satisfies the first threshold;
presenting a first feedback to the user in response to determining that the first amplitude associated with the first filtered signal satisfies the first threshold;
determining, by the one or more processors, from the plurality of instructions to monitor whether a second amplitude associated with the second filtered signal satisfies a second threshold;
determining, by the one or more processors, that the second amplitude associated with the second filtered signal satisfies the second threshold; and
presenting a second feedback to the user in response to a determination that the second amplitude associated with the second filtered signal satisfies the second threshold, the second feedback being different from the first feedback.

22. The method of claim 21, wherein the plurality of instructions indicates to monitor the first type of brain wave and the second type of brain wave.

23. The method of claim 21, further comprising determining, by the one or more processors, from the plurality of instructions to associate the first feedback with the first filtered signal so that the first feedback is generated in response to determining that the first amplitude associated with the first filtered signal satisfies the first threshold.

24. The method of claim 21, further comprising determining, by the one or more processors, from the plurality of instructions to select one of a plurality of soundtracks to be the first feedback and associate the first feedback with the first filtered signal so that the first feedback is generated in response to determining that the first amplitude associated with the first filtered signal satisfies the first threshold.

25. The method of claim 21, further comprising:
determining, by the one or more processors, from the plurality of instructions to associate a third feedback rather than the first feedback with the first filtered signal so that the third feedback rather than the first feedback is generated in response to determining that the first amplitude associated with the first filtered signal satisfies the first threshold; and
generating, by the one or more processors, the third feedback in response to determining that the first amplitude associated with the first filtered signal satisfies the first threshold.

26. The method of claim 21, wherein the first type of brain wave is an alpha wave, a beta wave, a theta wave, a delta wave, or a gamma wave.

27. The method of claim 26, wherein the first type of brain wave is the alpha wave, and the second type of brain wave is the theta wave.

* * * * *